(12) United States Patent
Patterson et al.

(10) Patent No.: US 11,311,322 B1
(45) Date of Patent: *Apr. 26, 2022

(54) LOAD SHARING BONE PLATE

(71) Applicant: Avanti Orthopaedics, LLC, Newarek, DE (US)

(72) Inventors: John Douglas Patterson, Newark, DE (US); Devanand Roshan Gooray, Chester Springs, PA (US); Bhismadev Cyrus Gooray, Needham, MA (US)

(73) Assignee: Avanti Orthopaedics, LLC, Wilmington, DE (US)

( * ) Notice: Subject to any disclaimer, the term of this patent is extended or adjusted under 35 U.S.C. 154(b) by 151 days.

This patent is subject to a terminal disclaimer.

(21) Appl. No.: 16/691,640

(22) Filed: Nov. 22, 2019

Related U.S. Application Data

(63) Continuation of application No. 15/049,137, filed on Feb. 21, 2016, now Pat. No. 10,517,657, which is a continuation-in-part of application No. 14/252,576, filed on Apr. 14, 2014, now Pat. No. 9,814,503.

(60) Provisional application No. 62/118,594, filed on Feb. 20, 2015.

(51) Int. Cl.
*A61B 17/80* (2006.01)

(52) U.S. Cl.
CPC ...... *A61B 17/8028* (2013.01); *A61B 17/8047* (2013.01)

(58) Field of Classification Search
CPC ............ A61B 17/1728; A61B 17/8028; A61B 17/8033; A61B 17/8047; A61B 17/808
See application file for complete search history.

(56) References Cited

U.S. PATENT DOCUMENTS

| 4,955,886 | A  | 9/1990  | Pawluk            |
| 5,578,034 | A  | 11/1996 | Estes             |
| 6,117,173 | A  | 9/2000  | Taddia et al.     |
| 6,692,503 | B2 | 2/2004  | Foley et al.      |
| 6,893,443 | B2 | 5/2005  | Frigg et al.      |
| 7,060,067 | B2 | 6/2006  | Needham et al.    |
| 7,179,260 | B2 | 2/2007  | Gerlach et al.    |
| 7,326,212 | B2 | 2/2008  | Huebner           |
| 7,695,473 | B2 | 4/2010  | Ralph et al.      |
| 7,981,142 | B2 | 7/2011  | Konieczynski et al. |
| 8,366,752 | B1 | 2/2013  | Jones             |
| 8,444,679 | B2 | 5/2013  | Ralph et al.      |
| 8,486,116 | B2 | 7/2013  | Hellman           |
| 2004/0158251 | A1 | 8/2004 | Morrison et al.  |
| 2006/0079900 | A1 | 4/2006 | Mathieu et al.   |

(Continued)

*Primary Examiner* — Anu Ramana
(74) *Attorney, Agent, or Firm* — Invention To Patent Services; Alex Hobson

(57) ABSTRACT

A load sharing bone plate has a plurality of directional apertures configured to effectively support and share the load with a fractured bone to promote healing. A load sharing bone plate may have a body portion that is thinner and be configured to be secured with smaller fasteners than conventional bone plates. A load sharing bone plate has a plurality of directional apertures, configured to direct a fastener is a specific orientation, such as in an oblique angle to the length and/or in an oblique angle to the width of the bone plate. A load sharing bone plate may be configured with a load sharing extension on at least one end that is configured to reduce stress concentration at the end of the bone plate. A load sharing extension may have a tapered thickness and/or width from the body portion to the extended end.

18 Claims, 17 Drawing Sheets

(56) References Cited

U.S. PATENT DOCUMENTS

| | | |
|---|---|---|
| 2006/0241607 A1 | 10/2006 | Myerson et al. |
| 2007/0276383 A1 | 11/2007 | Rayhack |
| 2008/0033437 A1 | 2/2008 | Shipp et al. |
| 2009/0248087 A1 | 10/2009 | Lewis |
| 2010/0016858 A1 | 1/2010 | Michel |
| 2010/0082070 A1 | 4/2010 | Diez |
| 2010/0234847 A1 | 9/2010 | Impellizzzeri |
| 2011/0087229 A1 | 4/2011 | Kubiak |
| 2011/0184470 A1 | 7/2011 | Gorek et al. |
| 2012/0083847 A1 | 4/2012 | Huebner |
| 2013/0090688 A1 | 4/2013 | Montella et al. |
| 2013/0096629 A1 | 4/2013 | Rollinghoff et al. |
| 2013/0150899 A1 | 6/2013 | Sixto, Jr et al. |

LOAD SHARING BONE PLATE

CROSS REFERENCE TO RELATED APPLICATION

This application is a continuation of U.S. patent application Ser. No. 15/049,137, filed on Feb. 21, 2016 and currently pending, which is a continuation in part of U.S. patent application Ser. No. 14/252,576, filed on Apr. 14, 2014, and issued as U.S. Pat. No. 9,814,503 on Nov. 14, 2017, and application Ser. No. 15/049,137 claims the benefit of provisional patent application No. 62/118,594, filed on Feb. 20, 2015; the entirety of all applications are hereby incorporated by reference herein.

BACKGROUND OF THE INVENTION

Field of the Invention

The present invention relates to bone plates.

Background

Bone plates are attached across a fractured bone to support and hold the bone in place as it heals. Bone plates are made out of rigid materials such as stainless steel and titanium, for example, and shield the fracture from stress. Stress shielding a fracture with a stiff reinforcing bone plate can result in longer healing times as the bone, and particularly the fractured portion of the bone, bears little to no load.

In addition, bone plates are usually truncated in a manner to cause high stress concentrations at the end or ends of the bone plate. After a fracture heals with the aid of a bone plate attachment, there is a risk of a new fracture at the end of the bone plate due to these high stress concentrations.

SUMMARY OF THE INVENTION

The invention is directed to a load sharing bone plate that is configured to effectively support a fractured bone while sharing the load with the bone to promote healing. A load sharing bone plate, as described herein, may have a body portion that is thinner than conventional bone plates and may have fasteners that are smaller than conventional fasteners. In an exemplary embodiment, a load sharing bone plate comprises a plurality of directional apertures, whereby a fastener configured therein is directed in a specific orientation through the bone. For example, a fastener may be directed in an oblique angle to the length axis of the bone plate, and in an oblique angle to the cross-length axis or across the width of the bone plate. In another exemplary embodiment, a load sharing bone plate comprises a load sharing extension on at least one end. A load sharing extension is configured to reduce stress concentration at the end of the bone plate and may comprise a tapered thickness and/or width from the body portion to the extended end of the load sharing extension. In still another embodiment, a load sharing bone plate is contoured to wrap around a portion of the bone. For example, a load sharing bone plate may have a bone contact surface that comprises a radius of curvature that substantially matches that of a bone that it is attached to. A load sharing bone plate may be used to repair any suitable type of bone fracture including long bone fractures, diaphyseal fractures, metaphyseal, epiphyseal, metadiaphyseal, intra articular, distal radius fractures and the like. In an exemplary embodiment, a load sharing bone plate is configured for a long bone fracture and has an aspect ratio of length to width of about 3.0 or more.

Proximal directional aperture, as used herein, is an aperture centrally configured along the length of a load sharing bone plate and configured to be proximal to a fracture when secured to a fractured bone. In one embodiment, a load sharing bone plate comprises two proximal directional apertures configured to be located on either side of a fracture and in one embodiment, a first proximal directional aperture is configured on first side of the load sharing bone plate and a second proximal directional aperture is configured on a second and opposing side.

Distal directional aperture, as used herein, is an aperture that is configured nearer the ends of a load sharing bone plate than a proximal directional aperture.

For brevity, the term bone plate is used synonymously with load sharing bone plate throughout the specification.

In an exemplary embodiment, a load sharing bone plate comprises a plurality of directional apertures that are configured to retain the bone plate with minimal fasteners. A directional aperture is configured to direct a fastener, secured therein, in a specific direction and in an exemplary embodiment, this direction is an oblique direction to the length axis of the bone plate and/or is an oblique direction to the width or cross-length axis of the load sharing bone plate. A directional aperture may be an integral directional aperture that comprises threads within the aperture to secure and retain a fastener in a specific direction to the bone plate. An integral directional aperture may have threads that are integral to the bone plate material, whereby the threads are cut into the bone plate material. In an alternative embodiment, an integral directional aperture comprises an insert that is affixed to the bone plate and may comprise threads in the insert material. The orientation of threads within a directional aperture may be configured to force a fastener, such as a screw in a pre-determined direction. In addition, the threads may be used by a guide, coupled thereto, to enable a pilot hole to be drilled through the bone in the pre-determined direction.

In another embodiment, a directional aperture may be configured to receive a separate insert, or combination of inserts, that can be configured to force a fastener in a desired orientation. In some embodiments, an insert comprises a softer material than the fastener, and a fastener inserted therethrough may form threads in the insert. For example, an insert may comprise a polyether ether ketone (PEEK) that is configured within a directional aperture. A fastener may be turned, or screwed through the PEEK insert and the male threads on the fastener may cut into the PEEK material to form female threads in the PEEK insert. Any suitable material may be used as an insert however. In one embodiment, an insert is configured with threads oriented to direct a fastener in a desired direction. An insert may be attached to the directional aperture or may be a separate piece that is situated in a directional aperture before a fastener is configured therein. In an exemplary embodiment, an insert is coupled to a directional aperture and may have a portion that extends over the top surface and/or bone contact surface of the load sharing bone plate.

In one embodiment, a load sharing bone plate comprises a pair of directional apertures that are configured for orientation with respect to a fractured bone, proximal to the bone fracture. These proximal directional apertures may be configured to be oriented on either side of fracture and in some cases the directional aperture may be configured to direct a fastener from a first side of a fracture to an opposing side of said fracture. In this manner, a fastener head may be retained in the load sharing bone plate on a first side of the fracture and the extended end of the fastener may be retained in the distal compact bone on the opposing side of the fracture. In addition, a proximal directional aperture may be configured to direct a fastener across the width of the bone plate wherein the head of the fastener is oriented in the proximal directional aperture on one side of the bone plate from a centerline and the extended end is retained in the distal compact bone on a second side from the centerline or at a width offset from the fastener head. The two proximal fasteners may be configured to cross each other as they extend from proximal directional apertures on either side of a fracture.

In an exemplary embodiment, a load sharing bone plate comprises a plurality of direction apertures that are configured for orientation with respect to a fractured bone, distal to the fracture, or at some offset distance from the fracture. A distal directional aperture may be configured to direct a fastener in an oblique angle to the length axis of the bone plate, and across the width. In an exemplary embodiment, a directional aperture is configured to direct a fastener in both an oblique angle to the length axis and in an oblique angle to the cross-length axis, or across the width. A first distal directional aperture may be configured near a first end of a bone plate and may be configured to direct a fastener toward the first end, and from a first side from a centerline toward a second side from the centerline. A second distal directional aperture may be configured near a second end of the bone plate and may be configured to direct a fastener toward the second end. and from the second side of centerline toward the first side from the centerline. In this manner, the two distal fasteners may more effectively secure the bone plate to the bone and thereby reduce the need for additional fasteners or fasteners of larger size. Additional apertures for fasteners may be configured in a load sharing bone plate, as described herein, between the proximal and distal directional apertures, as required.

The directional apertures, as described herein, may be configured to direct a fastener in any suitable direction, and, in an exemplary embodiment, a fastener is directed in a length angle, or angle along from the length axis of at least about 10 degrees, at least about 15 degrees, at least about 25 degrees, at least about 40 degrees and any range between and including the length angles listed. In an exemplary embodiment, a directional aperture is configured to direct a fastener across the width, or cross-length axis, at least about 10 degrees, at least about 15 degrees, at least about 25 degrees, at least about 40 degrees and any range between and including the width angles listed.

In one embodiment, a load sharing bone plate comprises a slotted aperture that is configured to receive a fastener. A slotted aperture may be configured to enable some alignment and orientation of a bone plate with one fastener already secured within the slotted aperture or within another aperture. In addition, a slotted aperture may be configured to cause a bone plate to move or slide as the fastener is tightened into the slotted aperture. For example, a first fastener may be attached through a first aperture in a bone plate on a first side of a fracture and then a second fastener may be secured through a slotted aperture configured on an opposing side of the fracture, whereby tightening of the second fastener in the slotted aperture pulls the bone plate in a way to bring the first aperture and first fastener toward the slotted aperture. In this manner, the fractured bone is pulled together in compression as the slotted fastener is tightened. A slotted aperture may be configured in any suitable location on a load sharing bone plate and in an exemplary embodiment is configured along the centerline and toward one end of the bone plate.

In an exemplary embodiment, a load sharing bone plate, as described herein, has a plurality of apertures consisting essentially of two proximal directional apertures, two distal directional apertures and one slotted aperture. The two proximal directional apertures may be configured to be oriented on opposing sides of a bone fracture. The two distal directional apertures may be configured on opposing ends of a bone plate.

The unique configuration of the directional apertures and fasteners configured therein enables a bone plate to have a reduced thickness and still effectively support the bone. For example, a conventional stainless steel bone plate may be 3.5 mm in thickness for a diaphyseal fracture repair and a load sharing bone plate of the present invention may have a body portion thickness of no more than about 3.0 mm, no more than about 2.75 mm, no more than about 2.5 mm and any range between and including the thickness values provided.

A load sharing bone plate may have any suitable geometry and in an exemplary embodiment comprises an elongated portion that has an aspect ratio of length to width of at least about 3.0 or more, at least about 4.0 or more, at least about 5.0 or more and the like. In one embodiment, a load sharing bone plate consists essentially of an elongated bone plate that has a width that is substantially no greater than the body portion length. An elongated bone plate may consist essentially of a body portion that has substantially a uniform width, load sharing extensions configured on either end, and a plurality of directional apertures, as described herein.

A load sharing bone plate may comprise a load sharing extension on one or both ends of the bone plate. A load sharing extension is an extension from a body portion that is configured to reduce stress concentrations between the end of the bone plate and the bone to which it is attached. A load sharing extension may be tapered in thickness and/or width from a body portion. For example, a body portion of a bone plate may have a substantially uniform thickness, such as having no more than a 25% variation in thickness or no more than a 10% variation in thickness, and a load sharing extension may have a thickness that tapers from the body portion to the extended end of the load sharing extension. In addition, a body portion of a load sharing bone plate may have a width and a load sharing extension may have a width that tapers from the body portion width to the extended end of the load sharing extension. Any suitable tapering geometry or contour may be used. A load sharing extension may have a length, as measured from the body portion end to the extended end, that is any suitable length. In an exemplary embodiment, the load sharing extension has a length that is about 1.25 times the body portion width or more, about 1.5 times the body portion width or more, about 2.0 times the body portion width or more, about 3.0 times the body portion width or more, and any range between and including the load sharing extension lengths provided.

A method is provided for bracing and supporting a fractured bone comprising the steps of attaching a load sharing bone plate, as described herein, to a fractured bone. In one embodiment, a load sharing bone plate comprises two proximal directional apertures configured for orientation with respect to a fractured bone, on either side of the bone fracture, two distal directional apertures configured near the ends of the bone plate and one slotted aperture. In an exemplary embodiment, the bone plate is oriented over the fracture with the two proximal directional apertures on either side of the fracture. The load sharing bone plate is attached to the fractured bone by first securing a fastener through a first distal directional aperture located on a first end, or the opposite end of the slotted aperture. A fastener is then inserted through the slotted aperture and secured. In an exemplary embodiment, the slotted aperture is configured to draw the bone plate secured by the first distal faster towards the slotted aperture, thereby compressing the fracture. A fastener is then secured through the proximal directional aperture on the first end of the bone plate. A fastener is then secured through the proximal directional aperture on the second end, the same end as the slotted aperture. Finally, a fastener is secured through the second distal directional aperture. The load sharing bone plate may have load sharing extensions on one or both ends. In addition, a pilot hole may be drilled in each of the directional apertures and slotted aperture prior to inserting and securing a fastener. A drill guide may be coupled the apertures in any suitable manner. In an exemplary embodiment, a guide is temporarily coupled to an aperture by the threads in the aperture.

In an exemplary embodiment, a load sharing bone plate comprises one or more multi-aperture inserts. An exemplary multi-aperture insert comprises two or more insert portions that extend into distinct and separate apertures in the bone plate and a coupling portion that couples the two insert portions together. The bone plate is configured around and between the two insert portions. An exemplary insert portion has an extended end that extends away from the coupling portion and into the aperture in the bone plate. In an exemplary embodiment, the extended end of the insert extends substantially to the surface of the bone plate. For example, a multi-aperture insert may comprise a coupling portion that extends along the bone contact surface of the bone plate and two insert portions that extend from the bone contact surface to the top surface of the bone plate, or the opposing surface to the bone contact surface, wherein the insert portions extend through the thickness of the bone plate.

A multi-aperture insert may be configured out of any suitable material including, but not limited to, metal, composites, plastically deformable materials including polymer, such as PEEK, polytetrafluoroethylene (PTFE), and other suitable polymers including fluoropolymers including TEFZEL® available from Dupont Inc., Wilmington, Del., and the like. A plastically deformable material is a material that can plastically deform and recover, whereby the material can be compressed or bent and then substantially return to an original shape or dimension.

In an exemplary embodiment, a multi-aperture bone plate consists essentially of a plastically deformable polymer, such as PEEK, and the bone plate is made out of metal. A multi-aperture insert preferably consists of a single piece of material, such a molded or machined single piece of PEEK. In an exemplary embodiment, a multi-aperture insert is press fit into a bone plate, wherein a portion of the multi-aperture insert may have to plastically deform to fit into the recess or aperture in the bone plate.

An insert portion may comprise one or more fastener apertures and may have any suitable shape. In one embodiment, an insert portion has only one fastener aperture and has a substantially cylindrically shaped outer surface. In another embodiment, an insert portion is configured with two fastener apertures and has a substantially hourglass shaped outer surface configured to fit within an corresponding hourglass shaped aperture in the bone plate. It is to be understood that any suitable shape may be utilized for an insert portion. The outer shape of the aperture and the corresponding outer shape of the insert portion may be configured to reduce the likelihood of the insert portion spinning when a fastener is inserted and screwed through the aperture. An insert portion with an hourglass shape, or having one substantially planar portion will more effectively resist spinning than a cylindrical shaped insert portion.

An insert portion may comprise a flange at the extended end of the insert. For example, an insert portion may have a flared end to provide more surface area of contact between the insert and the bone plate. This increased surface area may more effectively prevent the insert form twisting or spinning when a fastener is inserted therein. An insert portion may also comprise a beveled fastener aperture portion. A beveled fastener aperture may allow the head of a fastener to countersink into the insert and therefor enable the top surface of the fastener head to be substantially flush with the top surface of the bone plate.

A fastener aperture may be configured to direct a fastener in a direction that is non-parallel with the length axis of the insert portion, or in an oblique angle to the length and/or width of the bone plate. An exemplary multi-aperture insert portion may be configured to direct fasteners in such a way that the fasteners overlay along the width and/or length of the bone plate when the fasteners are secured to a bone. For example, a first fastener aperture may direct a first fastener such that the extended end of the first fastener, when configured in the fastener insert, overlaps with a second fastener configured in a second fastener aperture of a multi-aperture insert along the width and/or length axis of the bone plate, as depicted in FIGS. 1-3.

An insert portion may be configured at an offset angle to a perpendicular axis through the thickness of the bone plate. Put another way, an insert portion may be aligned with an offset fastener aperture axis that extends through the insert portion. In this embodiment, an insert portion may have to plastically deform in order for the multi-aperture insert to be inserted into the apertures of the bone plate as the two or more insert portions may not be parallel.

A coupling portion extends between the two separate and distinct insert portions and may be planar or have a non-uniform thickness between the two insert portions. A coupling portion extends along only one surface of the bone plate. For example, an exemplary multi-aperture insert is configured with the coupling portion configured in a recess in the bone plate along the bone contact surface and the insert portions extend up from the bone contact surface to the top surface of the bone plate.

There is a need for a bone plate that can effectively support a fracture and share some of the load with the bone during healing. There is a need for a bone plate that does not create a stress concentration at the termination end of the bone plate.

The summary of the invention is provided as a general introduction to some of the embodiments of the invention, and is not intended to be limiting. Additional example embodiments including, variations and alternative configurations of the invention, are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
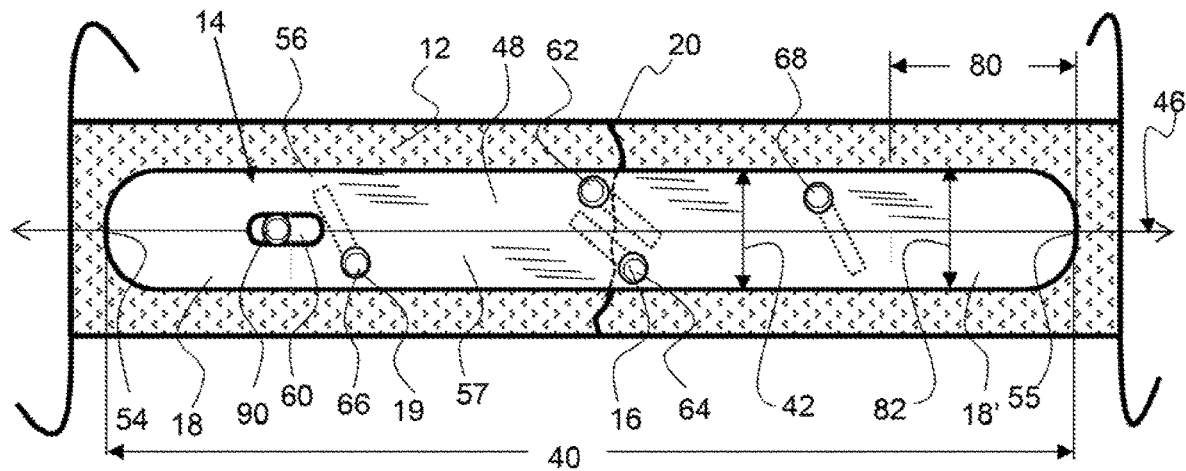

FIG. 1 shows a top-down view of an exemplary load sharing bone plate configured over a fractured bone.

Figure 2:
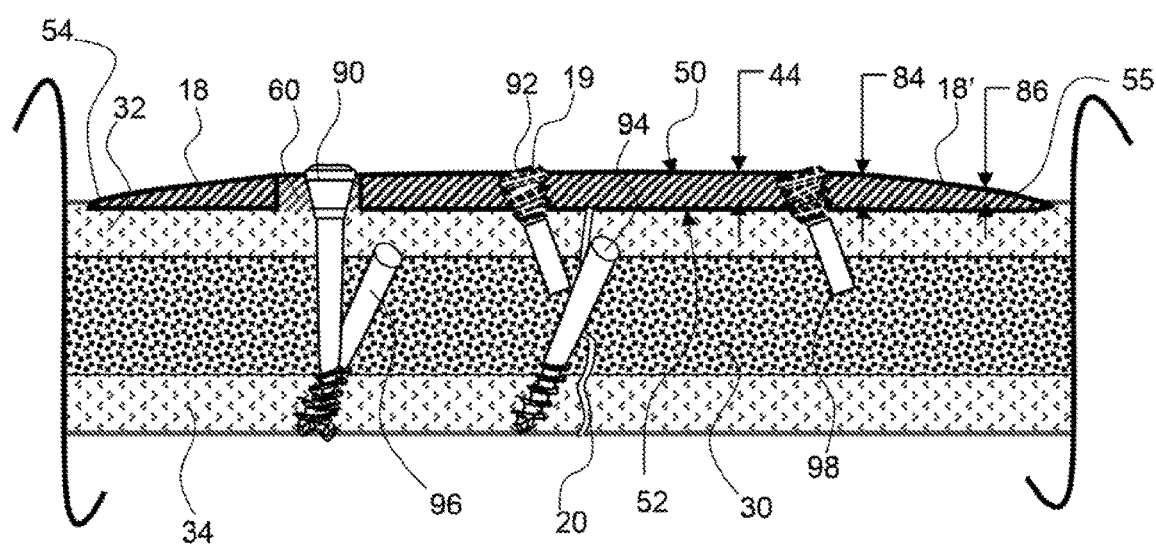

FIG. 2 shows a side cross-sectional view of the exemplary load sharing bone plate shown in FIG. 1, along the centerline 46.

Figure 3:
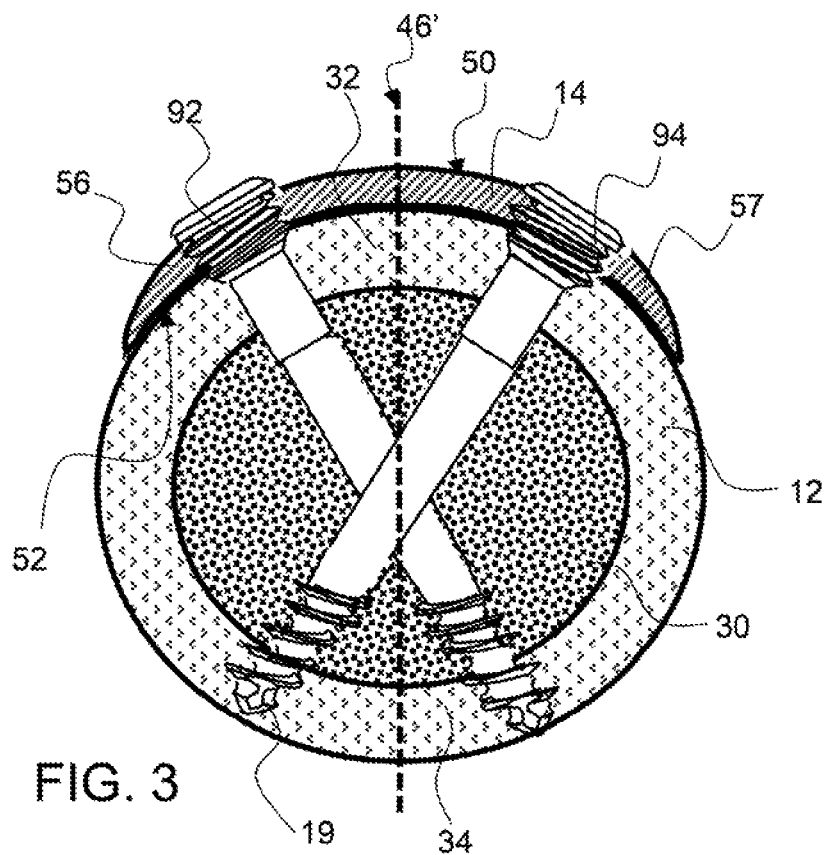

FIG. 3 shows a cross-sectional representation of the exemplary load sharing bone plate along a fracture.

Figure 4:
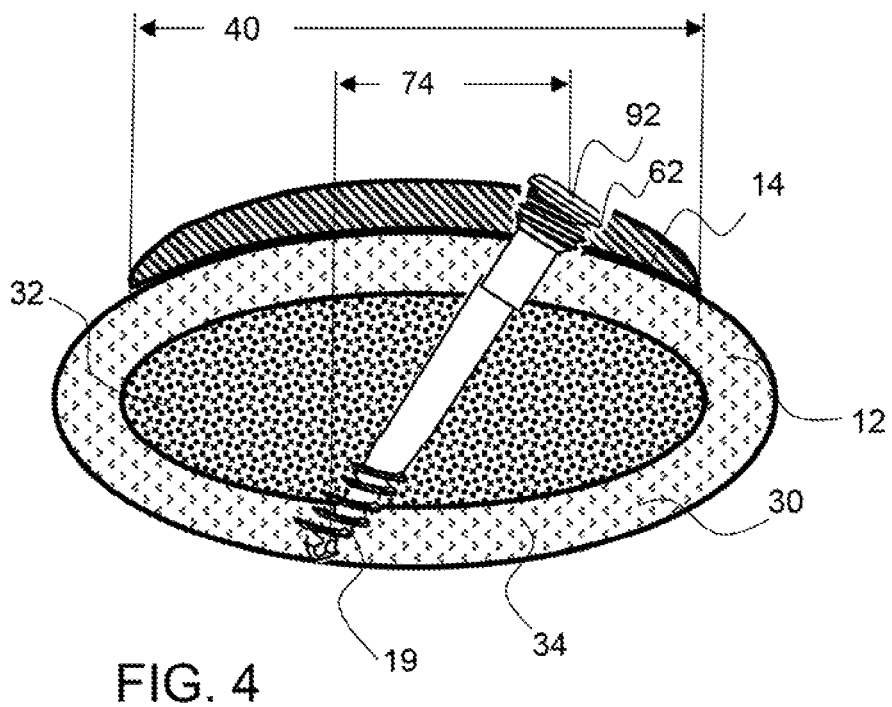

FIG. 4 shows a cross-sectional view of an exemplary load sharing bone plate having a distal directional aperture and a fastener secured therein.

Figure 5A:
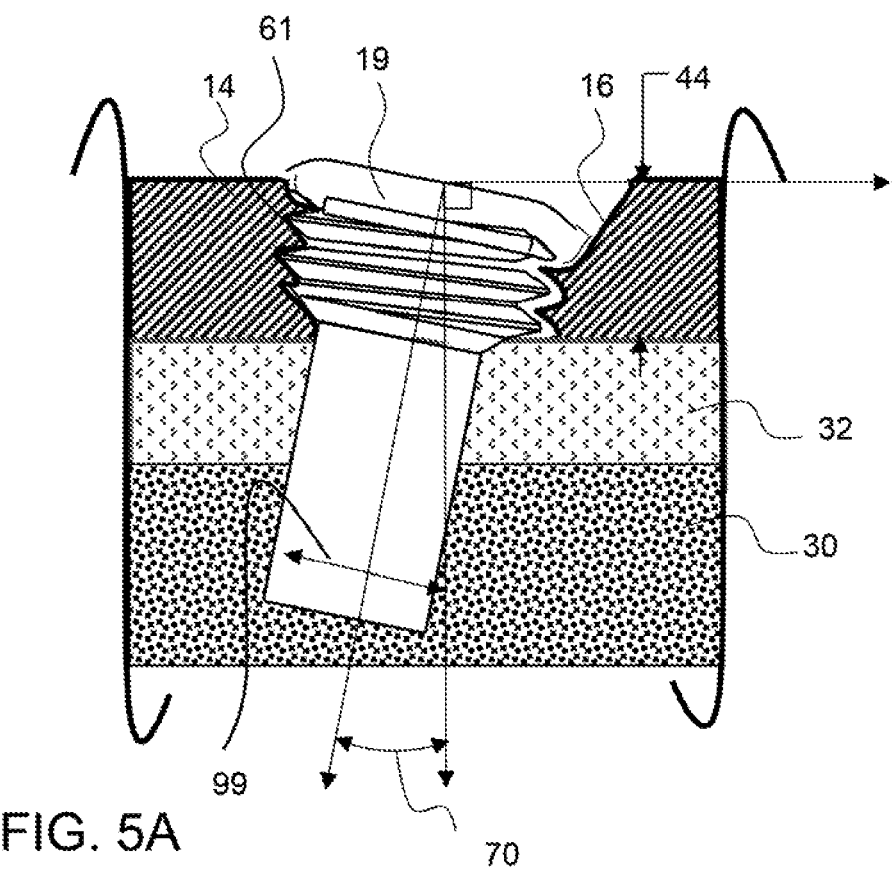

FIG. 5A shows a cross sectional view of an exemplary directional aperture having threads that engage with the threads of a fastener.

FIG. 58 shows a cross sectional view of an exemplary directional aperture having threads that engage with an insert configured within a directional aperture.

Figure 6:
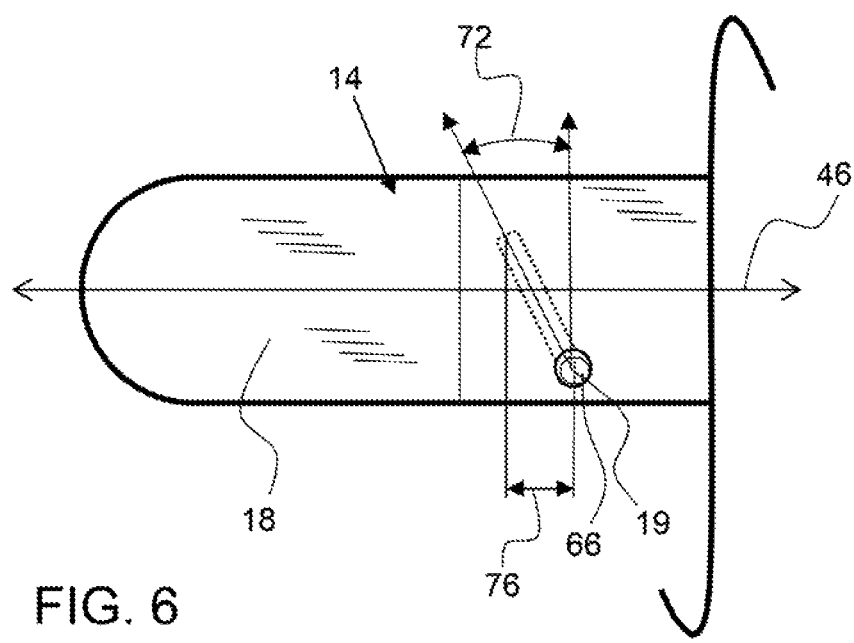

FIG. 6 shows a top-down view of an exemplary load sharing bone plate with a distal directional aperture having a fastener secured therein at a length angle.

Figure 7:
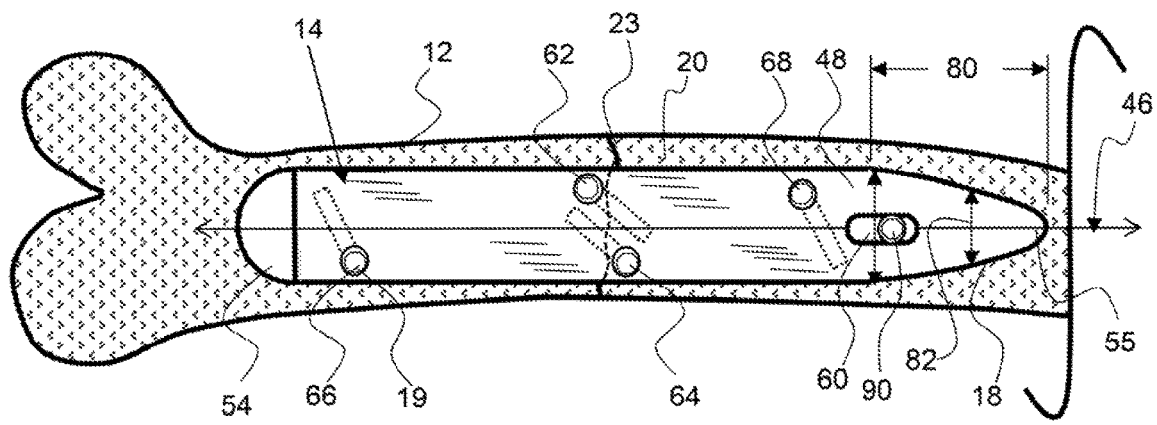

FIG. 7 shows a top-down view of an exemplary load sharing bone plate with a load sharing extension on a second end.

Figure 8A:
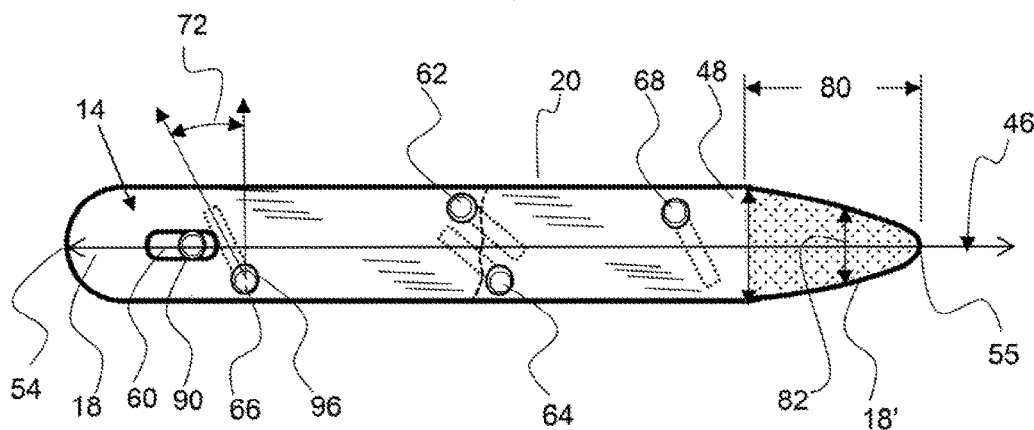

FIG. 8A shows a top-down view of an exemplary load sharing bone plate with a first distal directional aperture directing a first distal fastener at a length angle.

Figure 8B:
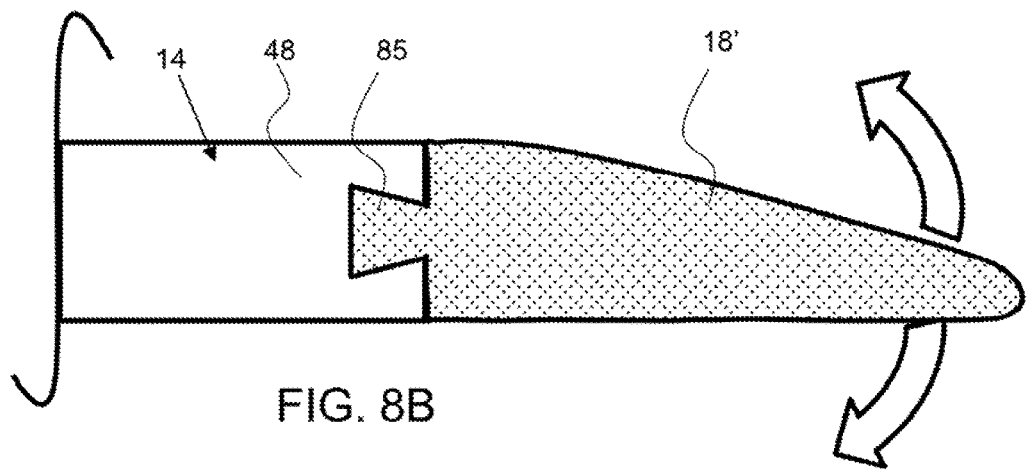

FIG. 8B shows a cross-sectional view of an exemplary load sharing extension coupled to the body portion of a load sharing bone plate.

Figure 9:
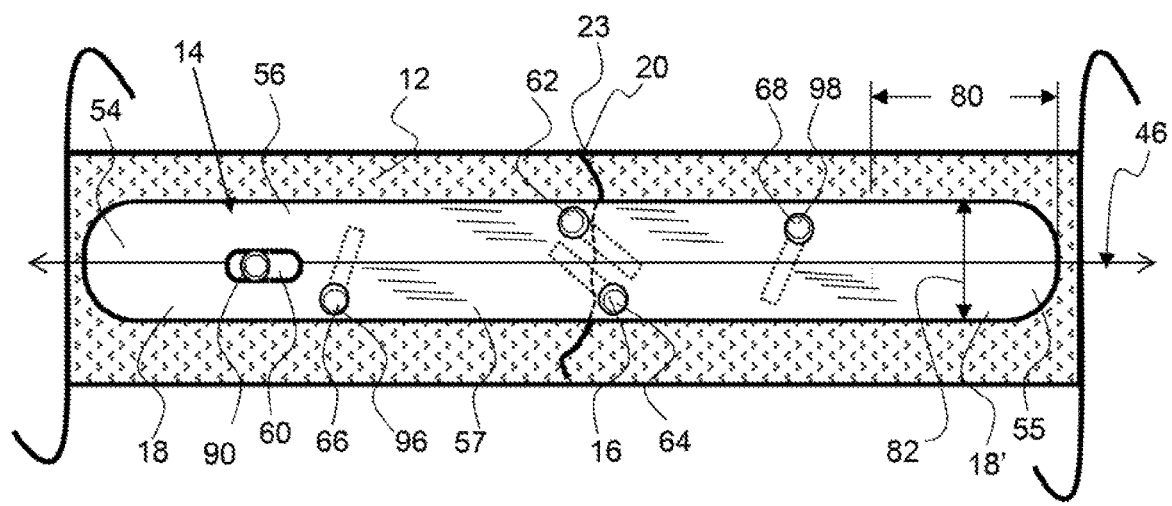

FIG. 9 shows a top-down view of an exemplary load sharing bone plate having load sharing extensions on both ends.

Figure 10:
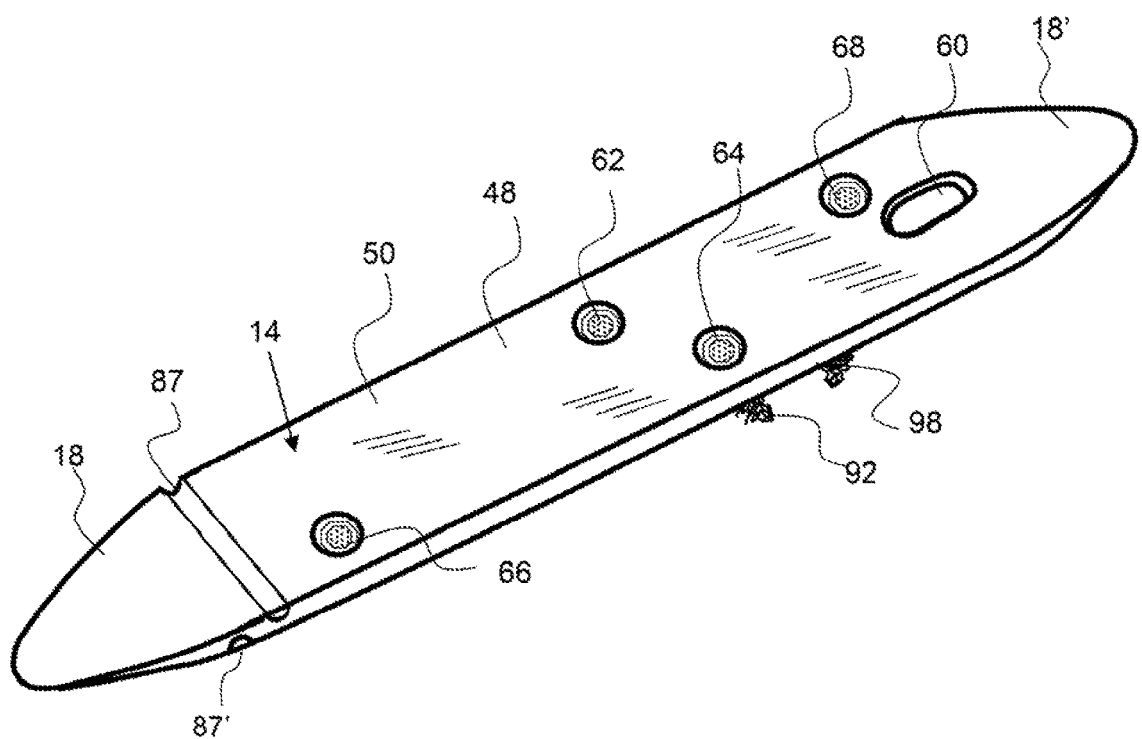

FIG. 10 shows an isometric view of an exemplary load sharing bone plate having two load sharing extensions.

Figure 11:
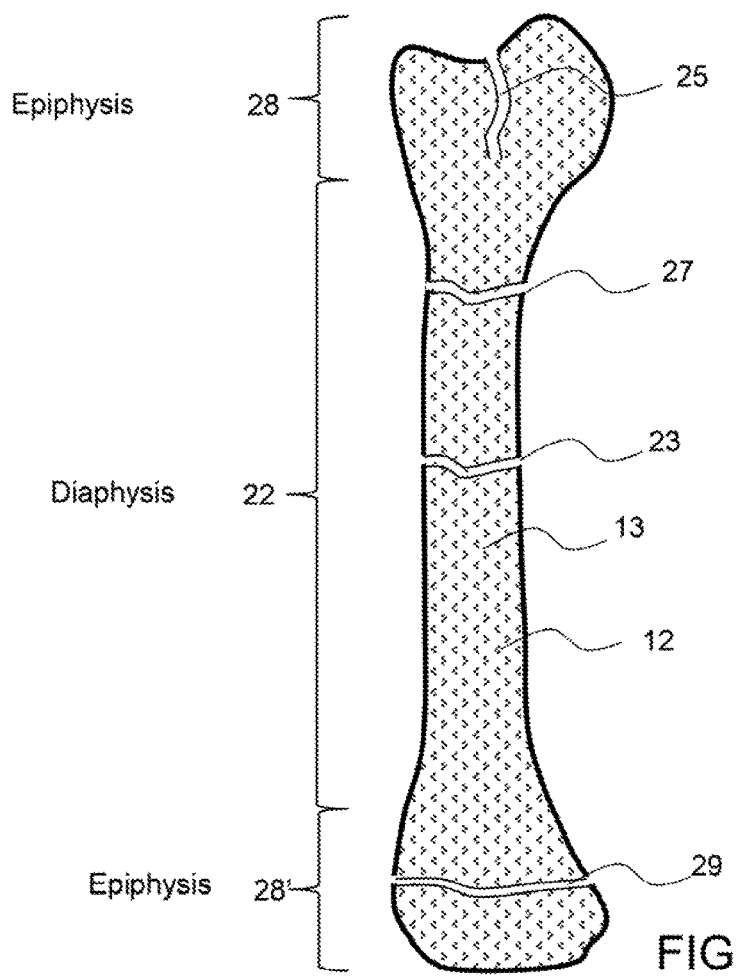

FIG. 11 shows bone depicting various types of fractures, including diaphyseal, metaphyseal, epiphyseal, and intra-articular fractures.

Figure 12:
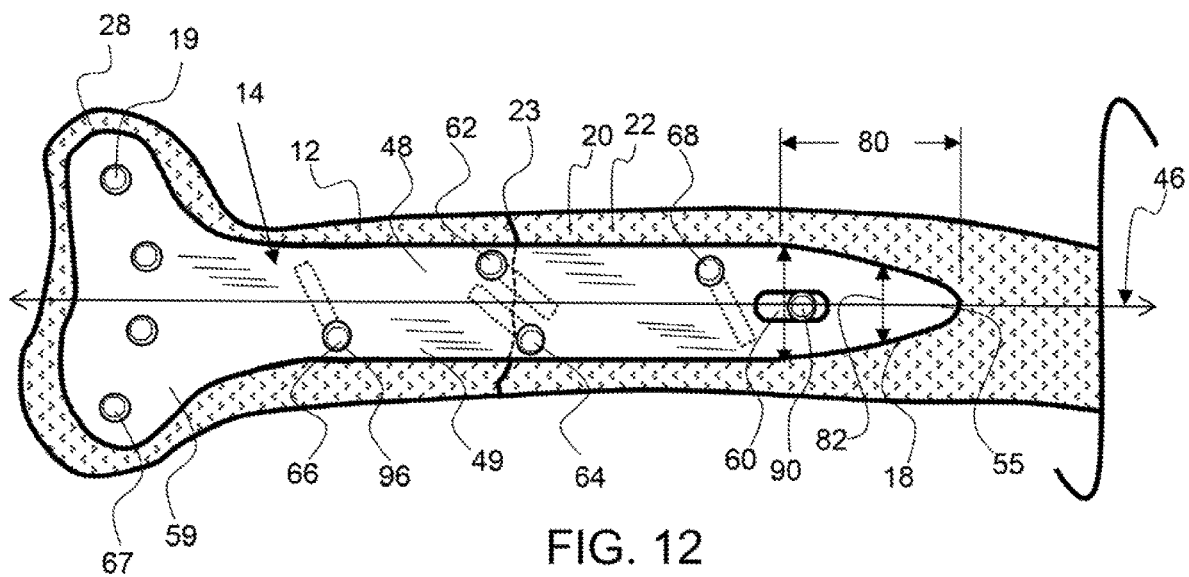

FIG. 12 shows a top-down view of an exemplary load sharing bone plate secured over a diaphyseal fracture and having an articulation fixation portion.

Figure 13:
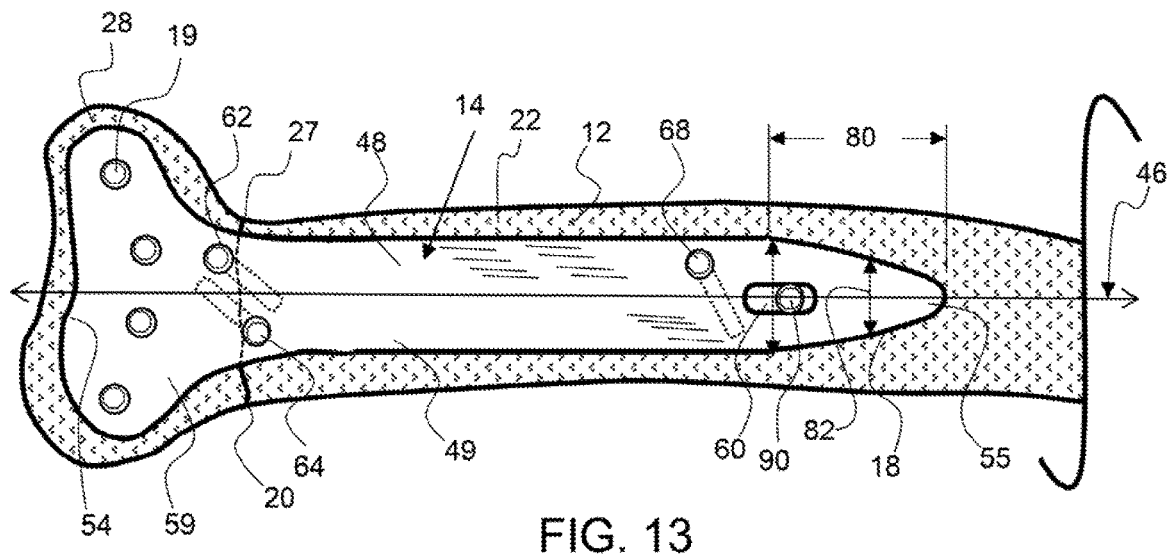

FIG. 13 shows a top-down view of an exemplary load sharing bone plate secured over a metaphyseal fracture and having an articulation fixation portion.

Figure 14:
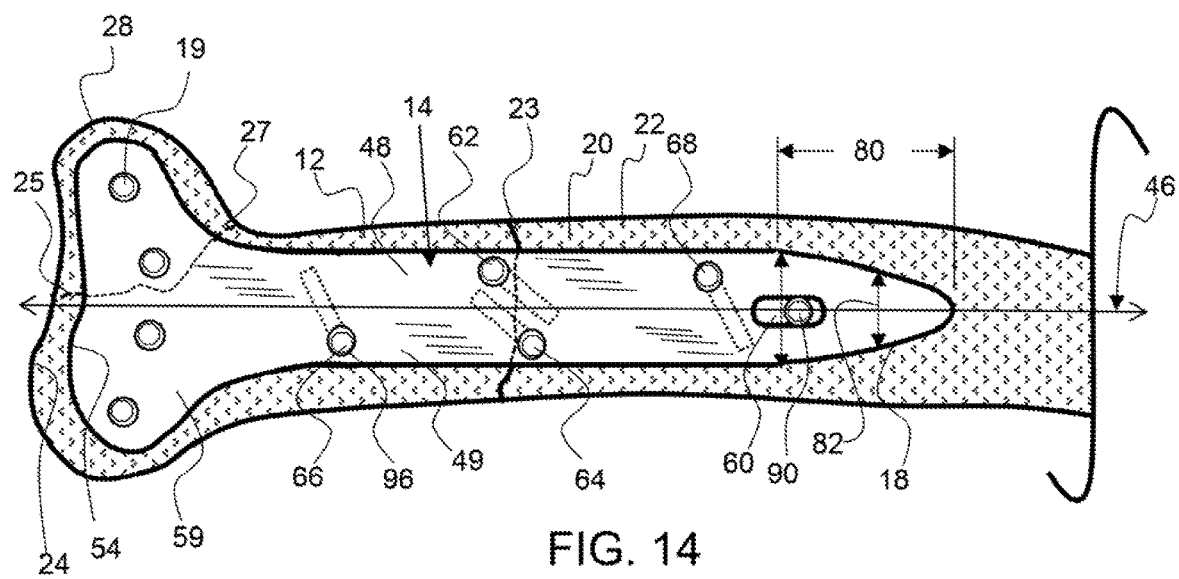

FIG. 14 shows a top-down view of an exemplary load sharing bone plate secured over a diaphyseal and metaphyseal fracture having an intra-articular extension into the joint.

Figure 15A:
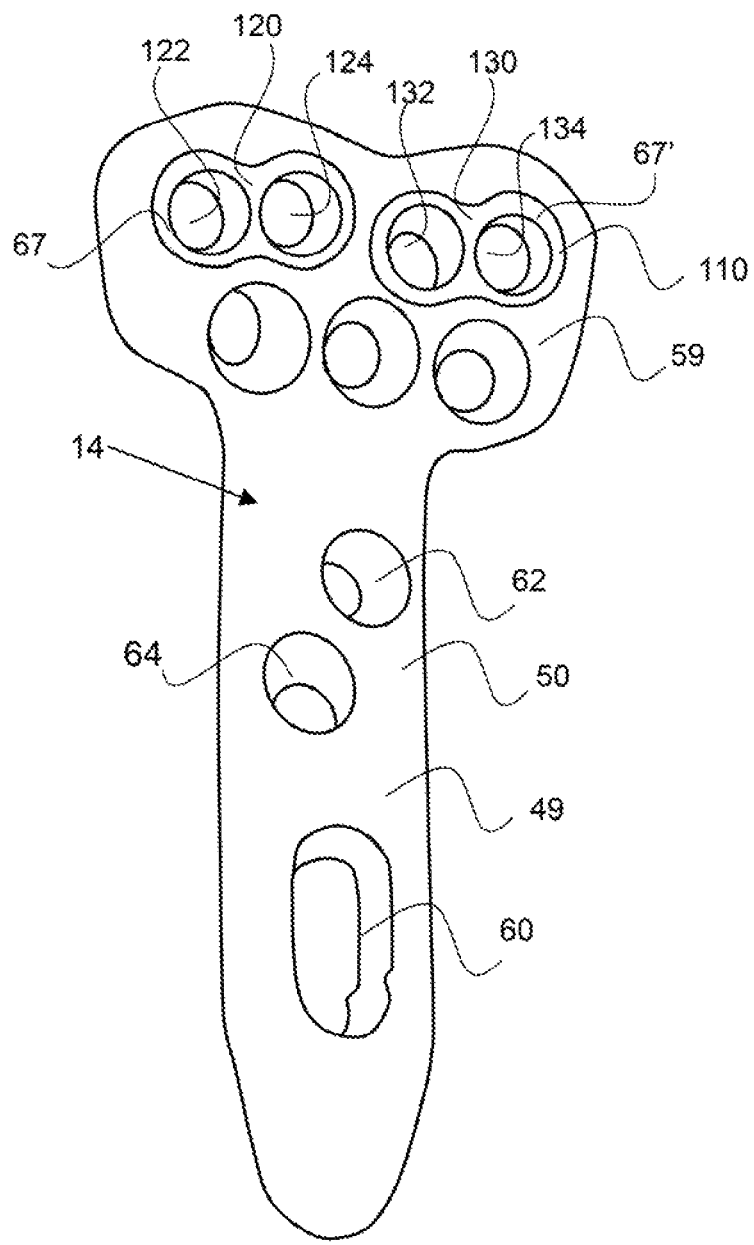

FIG. 15A shows a top perspective view of an exemplary load sharing bone plate having a multi-aperture insert configured in the articular fixation portion of the bone plate having two aperture insert portions, each with two fastener apertures.

Figure 15B:
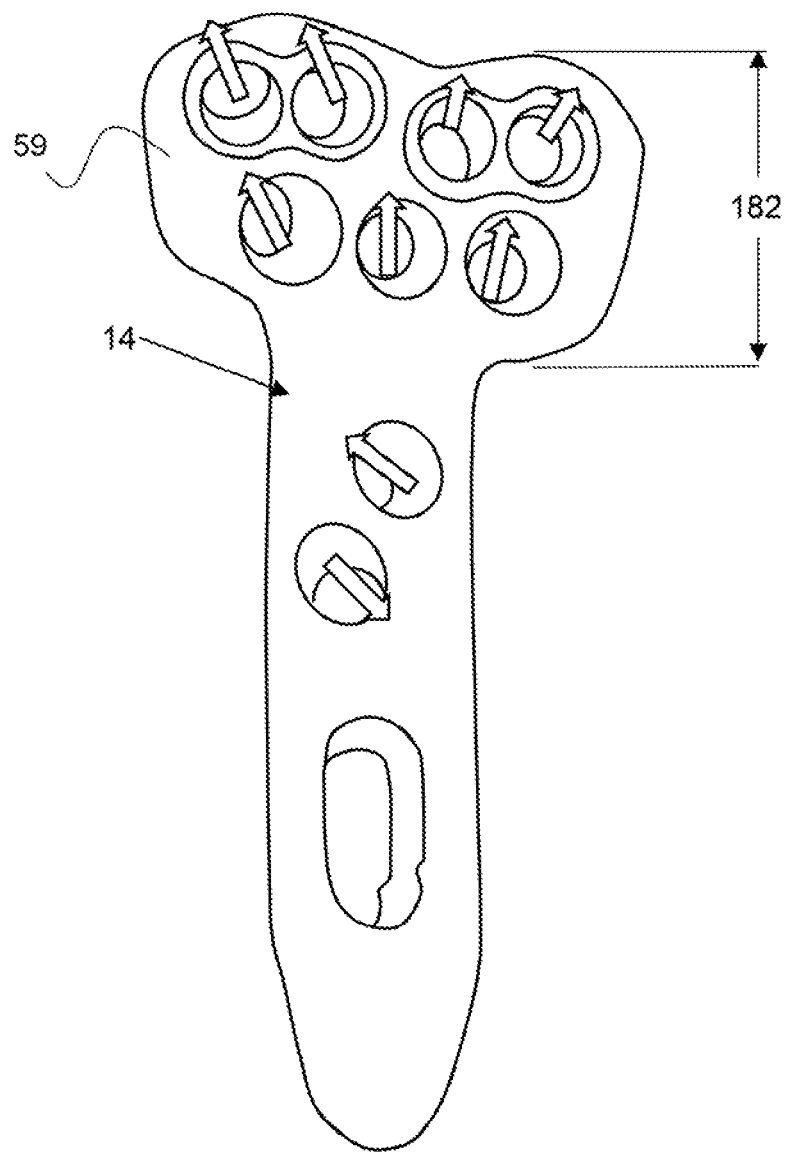

FIG. 15B shows a top perspective view of the exemplary load sharing bone plate shown in FIG. 15A with arrows indicating the direction that a fastener will be directed by the multi-aperture insert fastener apertures and other fastener apertures throughout the bone plate.

Figure 16:
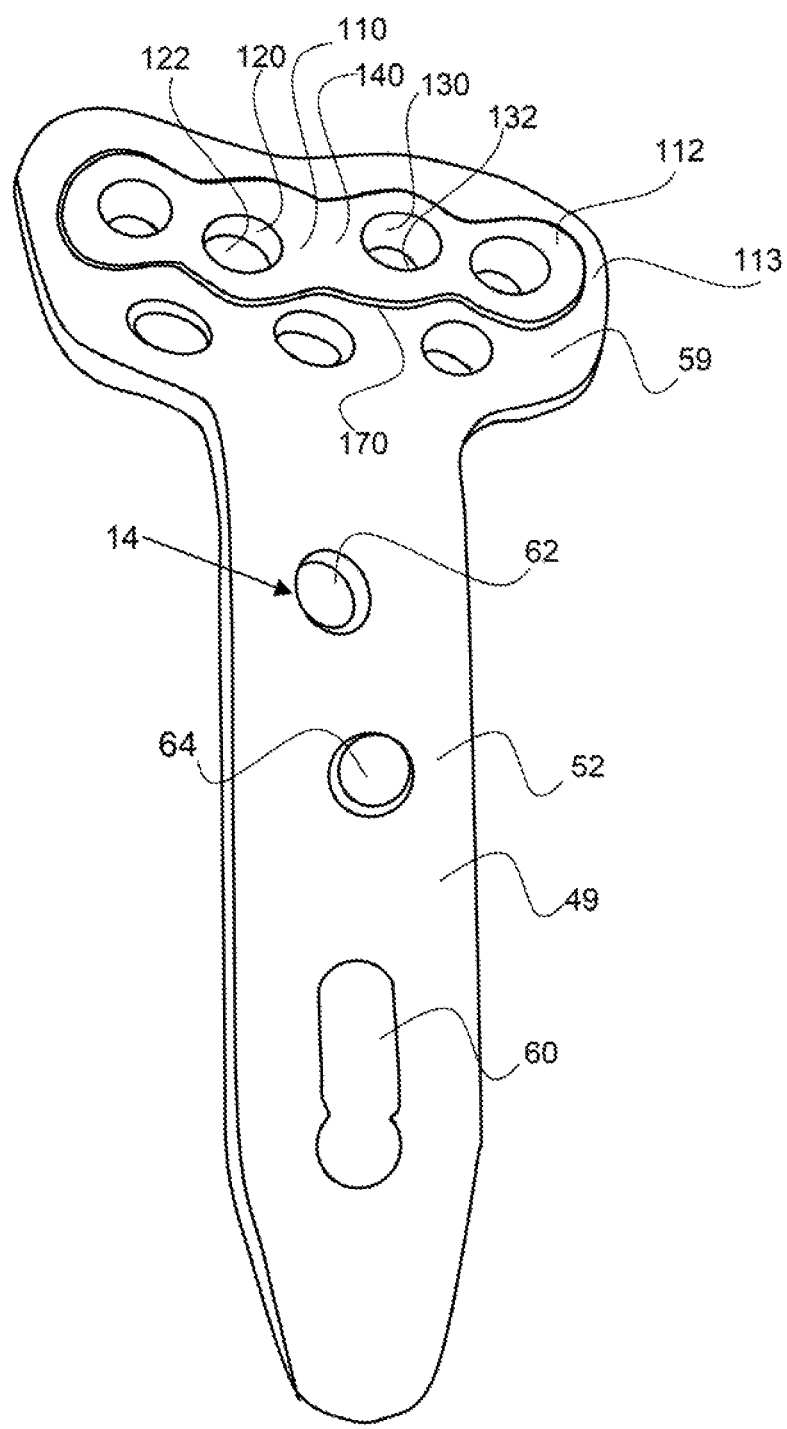

FIG. 16 shows a bottom perspective view of the exemplary load sharing bone plate shown in FIG. 16A having a multi-aperture insert configured in the articular fixation portion of the bone plate having a coupling portion extending between the two aperture insert portions.

Figure 17:
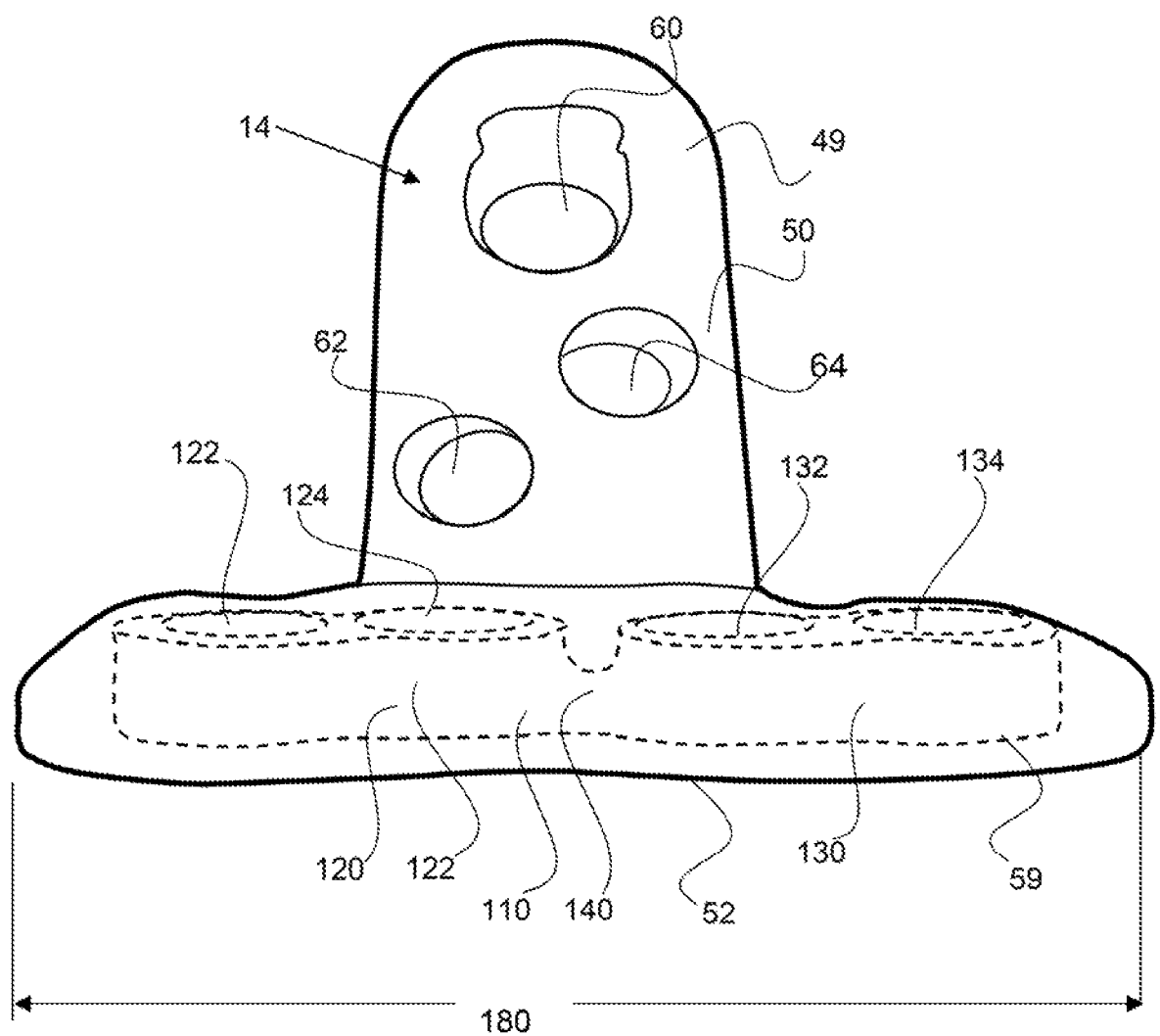

FIG. 17 shows an articular fixation end view of the exemplary load sharing bone place shown in FIGS. 15A and 16 having a coupling portion that extends between the two aperture insert portions.

Figure 18:
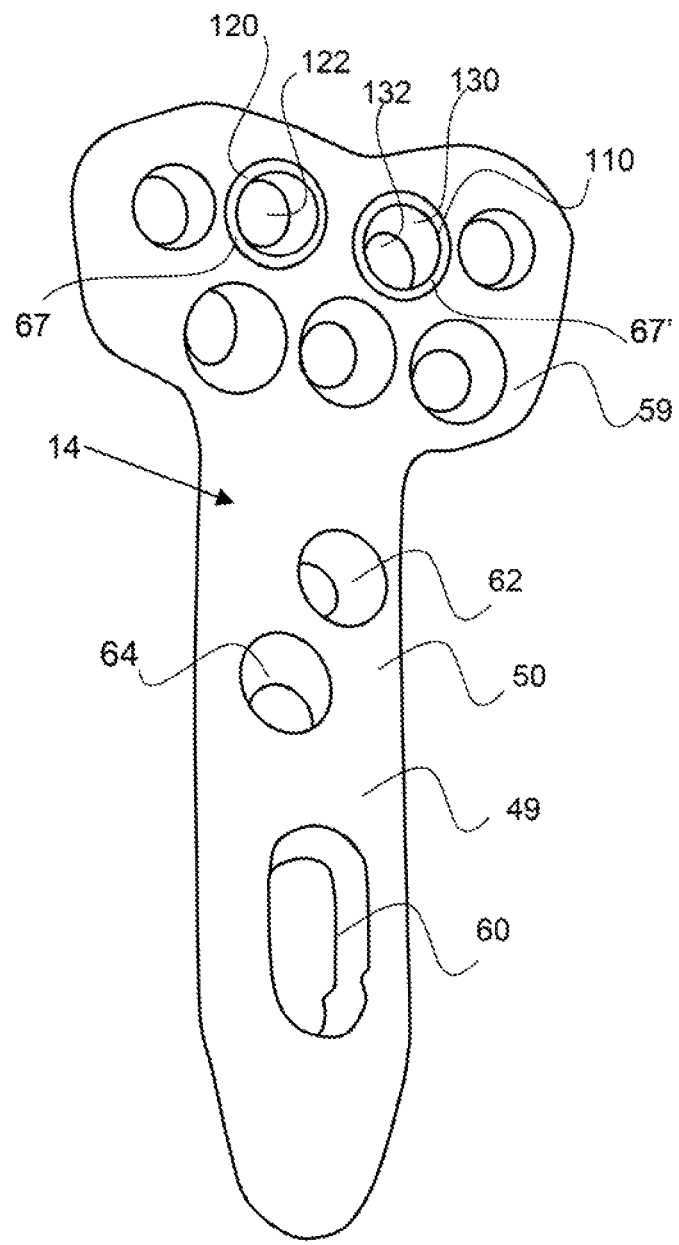

FIG. 18 shows a top perspective view of an exemplary load sharing bone plate having a multi-aperture insert configured in the articular fixation portion of the bone plate having two aperture insert portions, each with a single fastener aperture.

Figure 19:
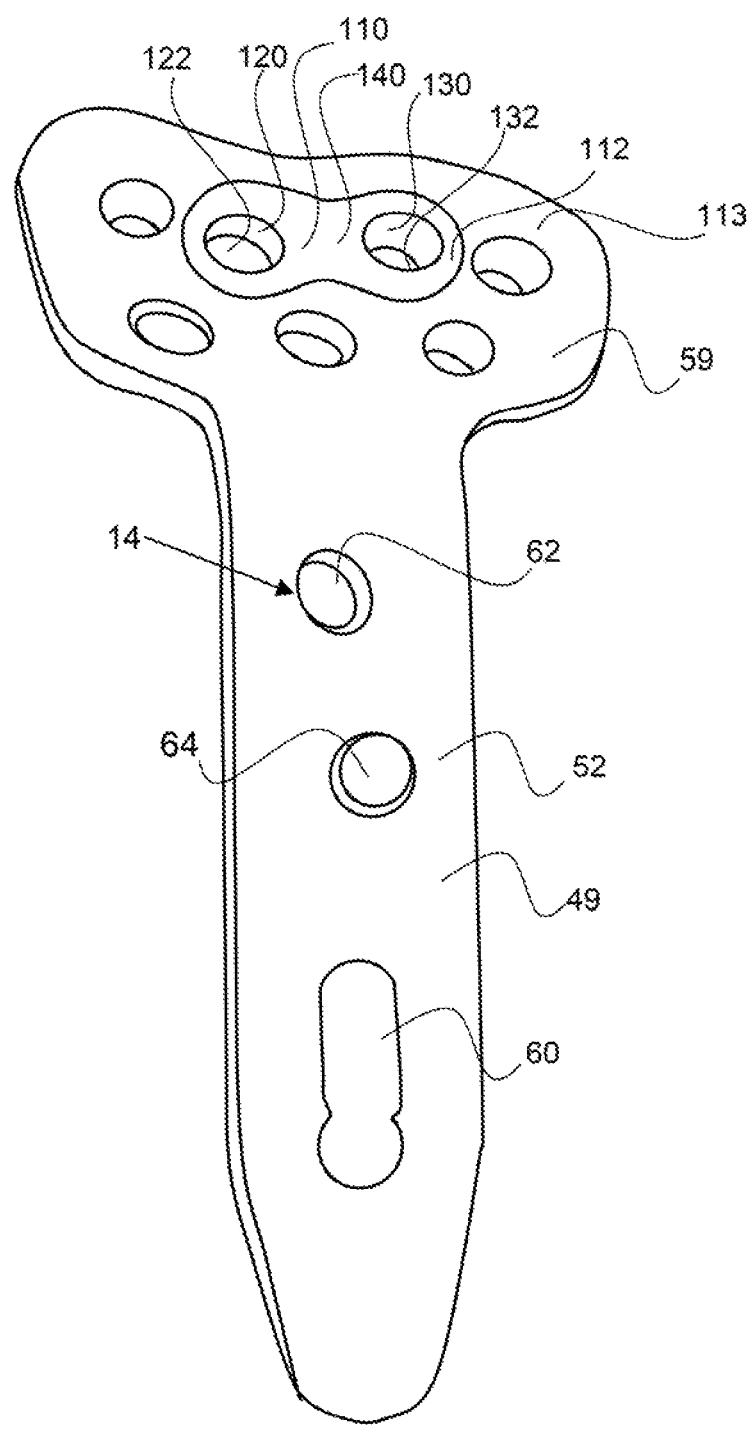

FIG. 19 shows a bottom perspective view of the exemplary load sharing bone plate shown in FIG. 18 having a multi-aperture insert configured in the articular fixation portion of the bone plate having a coupling portion extending between the two aperture insert portions.

Figure 20:
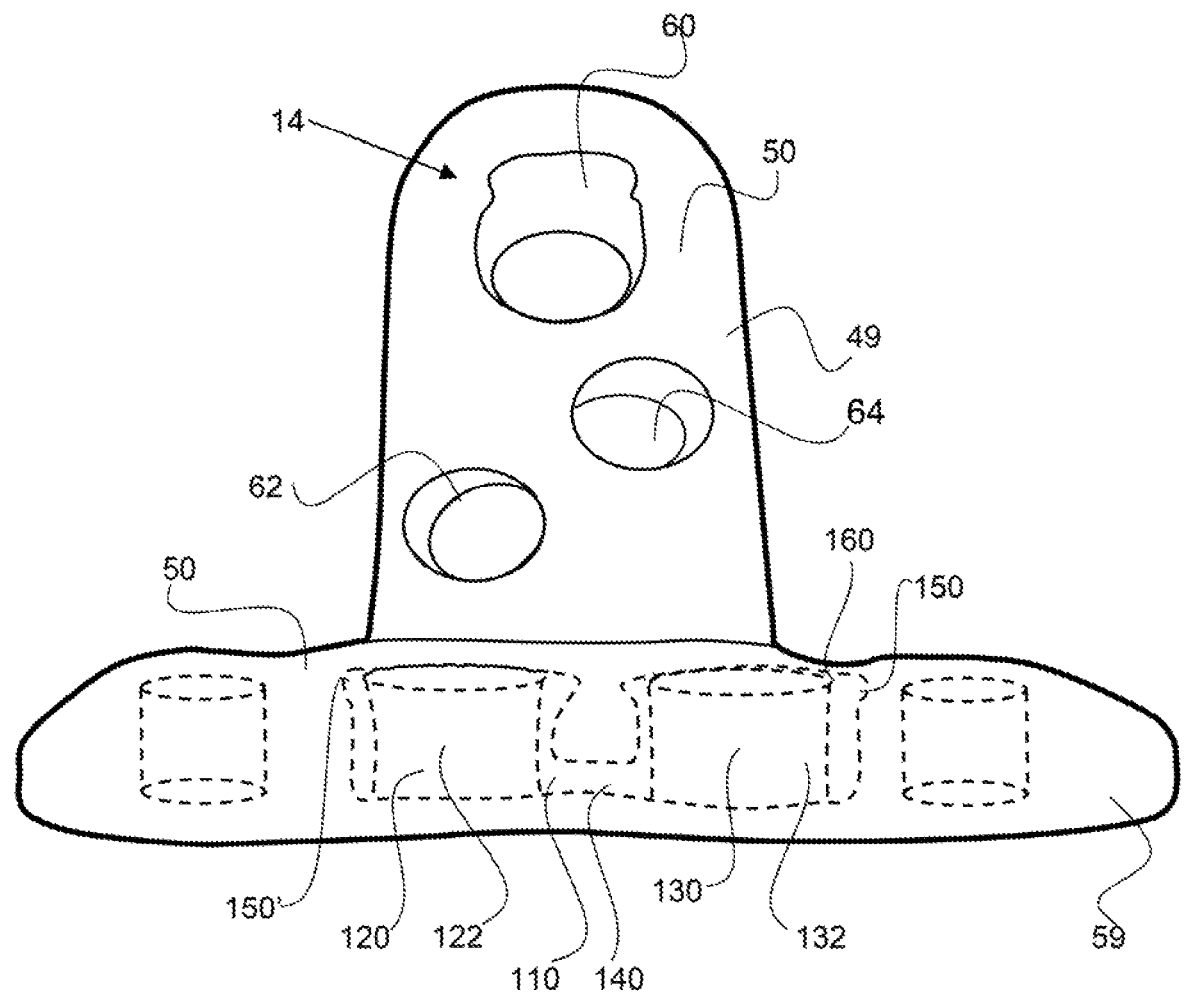

FIG. 20 shows an articular fixation end view of the exemplary load sharing bone place shown in FIGS. 18 and 19 having a coupling portion that extends between the two aperture insert portions.

Figure 21:
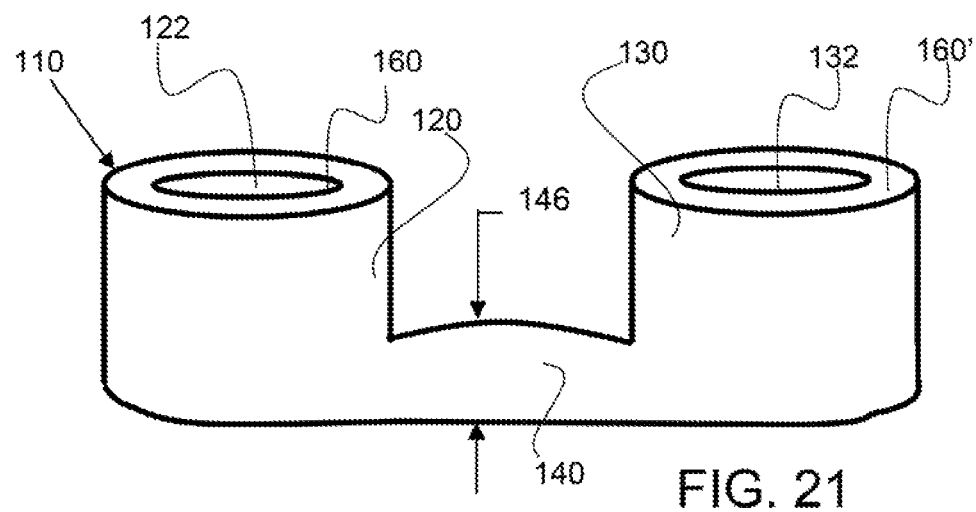

FIG. 21 shows a side perspective view of an exemplary multi-aperture insert having two aperture insert portions coupled together by a coupling portion that has a non-uniform thickness.

Figure 22:
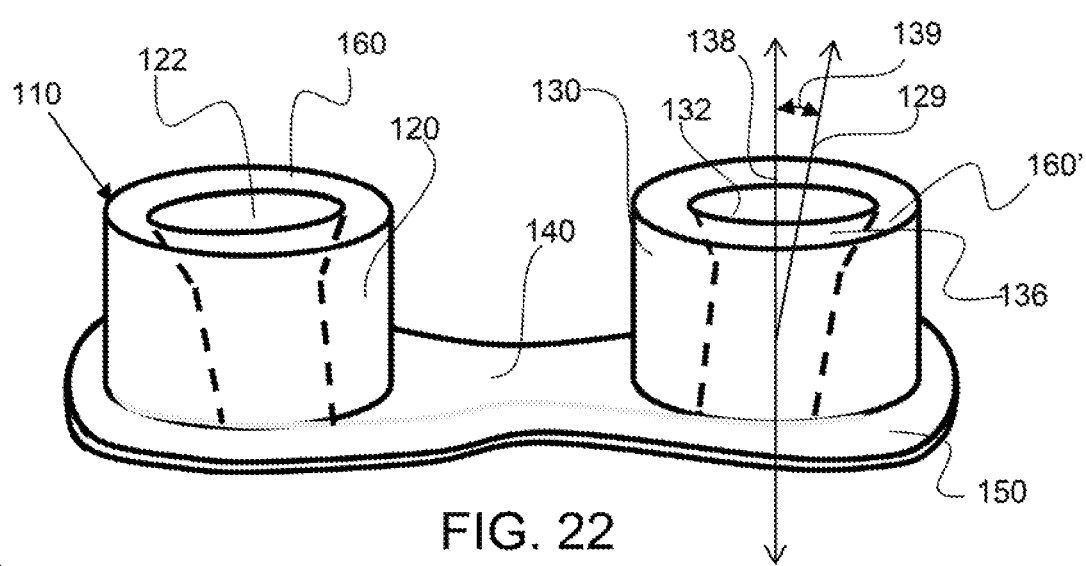

FIG. 22 shows a side perspective view of an exemplary multi-aperture insert having two aperture insert portions coupled together by a coupling portion is substantially planar and has a substantially uniform thickness.

Figure 23:
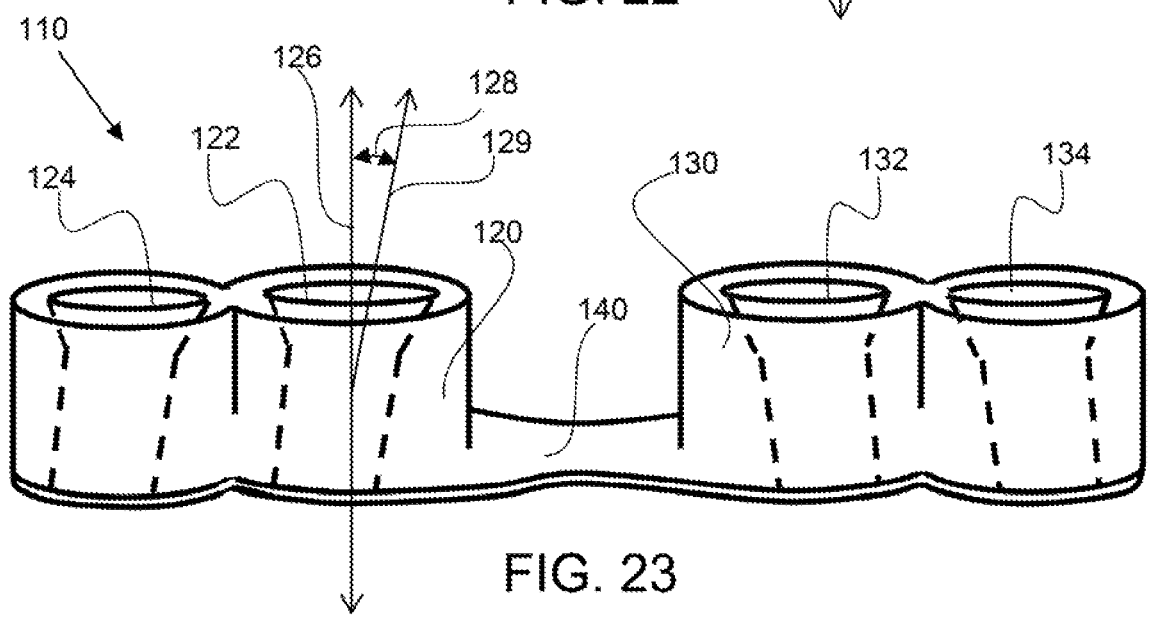

FIG. 23 shows a side perspective view of an exemplary multi-aperture insert having two aperture insert portions, each comprising two fastener apertures and a coupling portion that has a substantially uniform thickness therebetween.

Figure 24A:
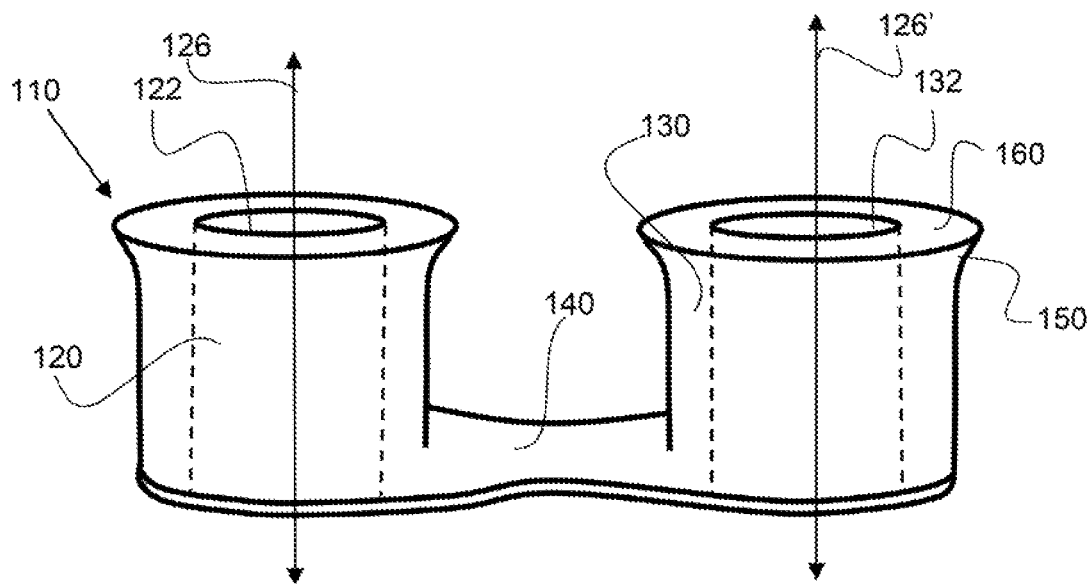

FIG. 24A shows a side perspective view of an exemplary multi-aperture insert having two aperture insert portions with flared extended ends coupled together by a coupling portion.

Figure 24B:
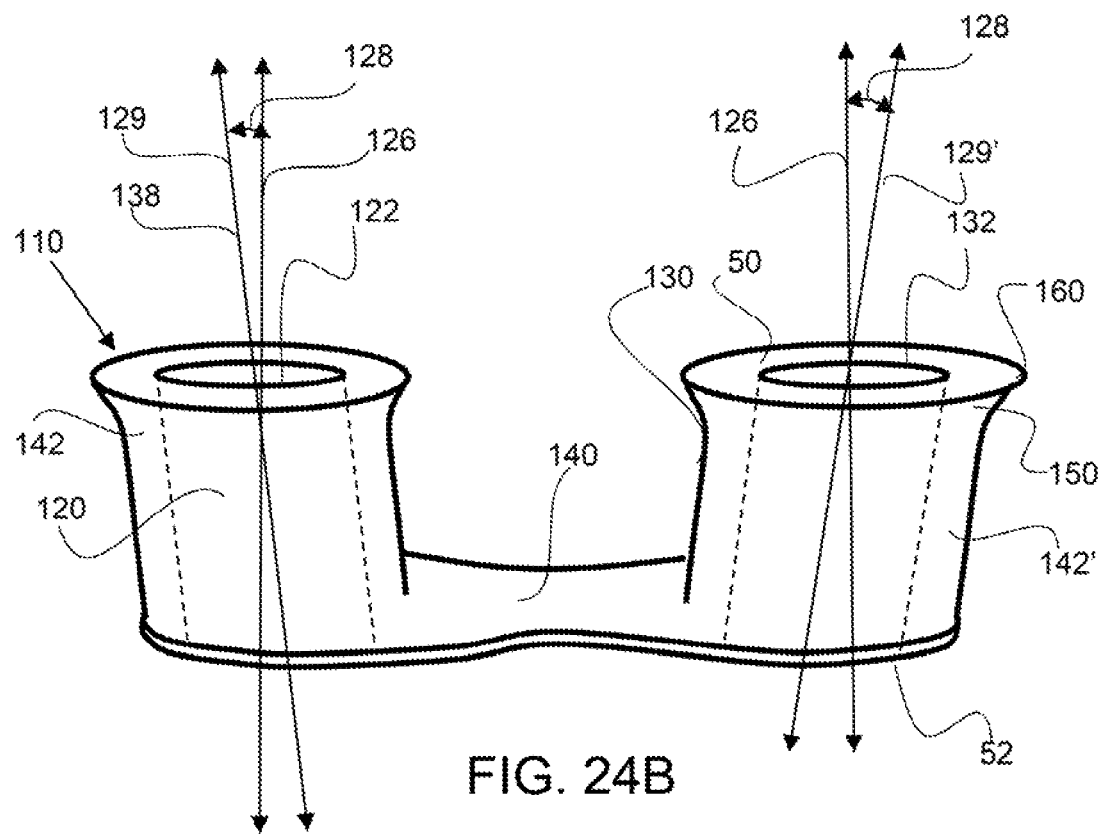

FIG. 24B shows a side perspective view of an exemplary multi-aperture insert having two aperture insert portions that are configured at offset angles.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale. Some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

As shown if FIG. 1, an exemplary load sharing bone plate 14 is configured over a fracture 20 in a bone 12. The load sharing bone plate has a substantially elongated shape with an aspect ratio of greater than 3:1, with the length 40 being at least three times greater than the width 42. The exemplary load sharing bone plate comprises stress sharing extensions 18, 18'. These stress sharing extensions have a length 80 that is greater than 1.25 the width 42 of the plate. The ends of the load sharing extensions are rounded and the width 82 of the load sharing extension at the interface with the body portion 48 of the bone plate is shown. The exemplary load sharing bone plate comprises a plurality of directional apertures 16 and a slotted aperture 60. The directional apertures have fasteners 19 configured therein, and the shaft of the fasteners are shown in dashed lines. A first proximal directional aperture 62 and second proximal directional aperture 64 are configured proximal and on opposing sides of the fracture 20. The first proximal directional aperture 62 is on a first side 56 from the centerline 46 of the bone plate and proximal to a first end 54 from the bone fracture 20. The second proximal directional aperture 64 is configured on a second side 57 from the centerline and proximal to the second end 55 from the bone fracture. The fasteners configured therein span across the fracture and are configured at oblique angles to both the width and length of the bone plate. A first distal directional aperture 66 and second distal directional aperture 68 are configured nearer the first end 54 and second end 55 of the bone plate, respectively. The fastener in the first distal directional aperture extends toward the first end 54 and across the width from a second side 57 toward a first side 56 from the centerline of the bone plate. The fastener in the second distal directional aperture 68 extends toward the second end 55 and across the width from a first side toward a second side from the centerline of the bone plate. A slotted fastener 90 is configured in the slotted aperture 60 and is not configured in any substantially oblique angle to the width or length of the bone plate.

As shown in FIG. 2, the exemplary load sharing bone plate 14 shown in FIG. 1, has a plurality of fasteners that extend across the centerline 46 of the bone plate. The first proximal fastener 92, configured in the first proximal directional aperture extends from a first side toward a second side, and toward the second end 55. The second proximal fastener 94 configured in the second proximal directional aperture, not shown, extends from a second side toward the first side, and toward the first end 54. In this embodiment, the first and second proximal directional apertures extend across the fracture 20 and are configured to extend through the proximal compact bone 32, or compact bone adjacent to the bone contact surface 52 of the load sharing bone plate 14, and secure into the distal compact bone 34, or the compact bone opposite the bone plate. The first slotted fastener 90 is configured in the slotted aperture 60 and has a beveled head that seats within the slotted aperture. The first distal fastener 96 extends from a second side toward the first side and toward the first end 54. The second distal fastener 98 extends from the first side toward the second side, and toward the second end 55. In an exemplary embodiment, one or more of the fasteners has threads on the extended end to secure the fastener in the distal compact bone 34.

As shown in FIG. 3, an exemplary load sharing bone plate 14 has a contoured geometry that is configured to align with the outer bone surface. The top surface 50 and the bone contact surface 52 of the bone plate are both configured with a contour to that matches the outer contour of the bone and provides a substantially uniform thickness bone plate. FIG. 3 is a representation of the exemplary proximal fasteners 92 and 94 extending through a bone where they are secured in the distal compact bone 34. In this exemplary embodiment, the two distal fasteners cross each other within the bone as they extend from one side of the bone plate to an opposing side of the bone plate. The centerline 46' of the bone plate is indicated by the dashed line extending through the load sharing bone plate 14 and bone 12.

As shown in FIG. 4, an exemplary load sharing bone plate 14 has a distal directional aperture 62 and a distal fastener 92 secured therein. The load sharing bone plate has less of a contour than the load sharing bone plate shown in FIG. 3. Any suitable contour may be configured in one or more surfaces of a load sharing bone plate as described herein. The load sharing bone plate 14 shown in FIG. 4, has a width 40 and the fastener 92 has a width offset 74 that is the displacement width between the head of the fastener and the extended end of the fastener as measured across the width axis of the bone plate.

As shown in FIG. 5A, an exemplary load sharing bone plate 14 is configured with a directional aperture 16 having threads 61 that engage with the threads of the fastener 19. The width angle 70 is the offset angle of the length axis of the fastener from a perpendicular line drawn through the head of the fastener when secured in the directional aperture 16. The thickness of the bone plate 44 is shown in FIG. 5A.

Figure 5B:
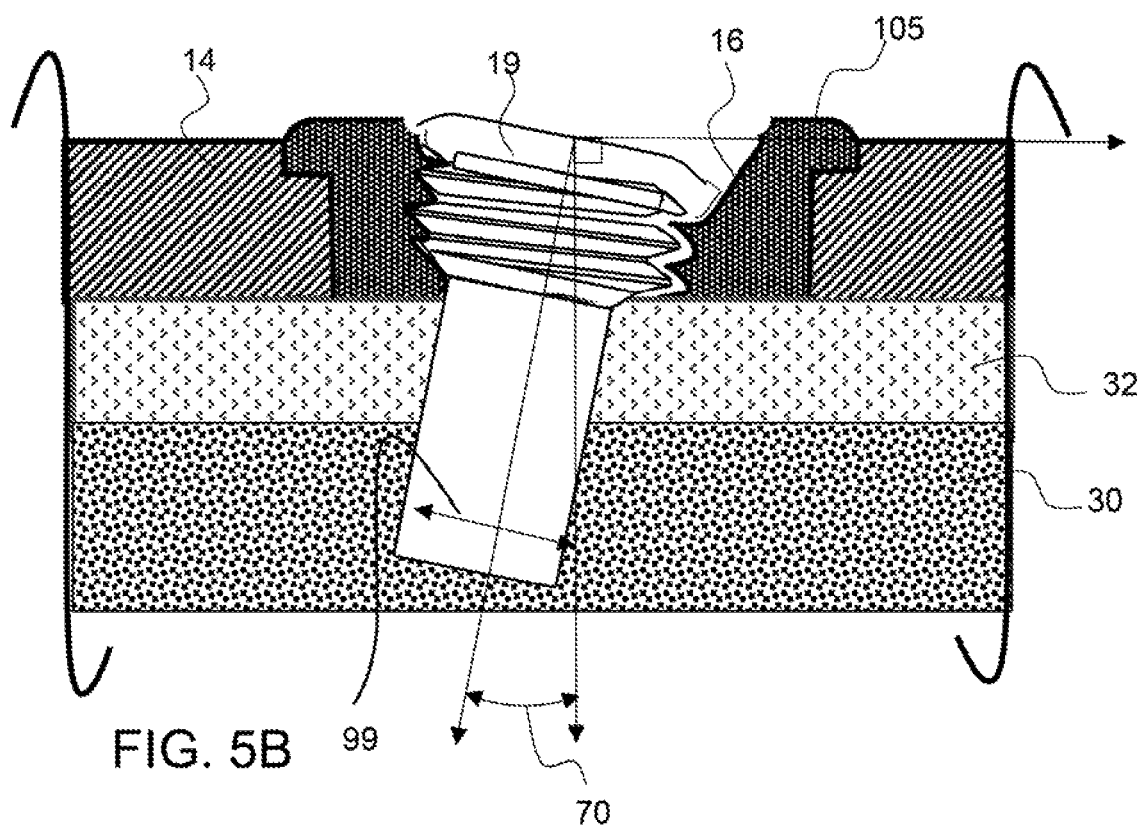

As shown in FIG. 5B, an exemplary load sharing bone plate 14 is configured with a directional aperture 16 having an insert 105 configured therein. In one embodiment, the fastener 19 is configured to cut threads into the insert as it is screwed through the insert. The insert 105 shown in FIG. 5B extends beyond the top surface of the load sharing bone plate 14 but may be recessed whereby the insert is flush with the top surface of the bone plate. An insert may extend beyond the bone contact surface of the bone plate as well. An insert may have any suitable geometry to secure and couple an insert to the bone plate.

As shown in FIG. 6, an exemplary load sharing bone plate 14 has a distal directional aperture 66 having a fastener 19 secured therein at a length angle 72, or the offset angle of the length axis of the fastener from a line extending through the head of the fastener and extending in a cross-length axis direction. The length offset 76, or the distance that the extended end of the faster extends from the head of the fastener along the length axis, is shown.

As shown in FIG. 7, an exemplary load sharing bone plate 14 has a load sharing extension 18 on a second end 55. The exemplary load sharing extension tapers in the width dimension from the body portion 48 to the extended end. A load sharing extension may comprise notches, slits or other stress relieving features that extend in any suitable direction including along the length and/or width of the bone plate. The first end 54 of the load sharing bone plate has a rounded geometry. FIG. 7 shows an exemplary load sharing bone plate configured as a diaphyseal fracture bone plate consisting essentially of a body portion having a substantially a uniform width and a load sharing extension on a second end.

As shown in FIG. 8A, an exemplary load sharing bone plate 14 has a first distal directional aperture directing a first distal fastener at a length angle 72. The first end 54 of the load sharing bone plate is configured with a load sharing extension 18 having a first geometry and the second end 55 is configured with a second load sharing extension 18' having a second and different geometry. The width 82 of the second load sharing extension 18' is reduced along the length of the load sharing extension from the body portion 48 to the extended end. The slotted aperture is configured along the centerline and distal the fracture from the first distal directional aperture 66. As shown in FIG. 5A, the load sharing extension 18' is made of a material that is different from the material of the body portion 48. The load sharing extension may be coupled to the body portion through any suitable means including an interference fit coupling, adhesive, welding and the like. In an exemplary embodiment, a load sharing extension consists essentially of a different material than the body portion of the load sharing bone plate. For example, a load sharing extension may be made out of PEEK and the body portion of the load sharing bone plate may be made out of stainless steel or titanium. In another embodiment, a load sharing extension is made out of a softer or more flexible metal than the body portion of the load sharing bone plate.

As shown in FIG. 8B, the load sharing extension 18' is coupled to the body portion 48 of the load sharing bone plate 14 through an interference fit coupler 85. A coupler, such as the interference fit coupler 85 shown in FIG. 88 may also act as a flex feature, whereby the load sharing extension can flex as indicated by the large arced arrow.

As shown in FIG. 9, an exemplary load sharing bone plate 14 has load sharing extensions on both ends. A first distal directional aperture 66 directs a first distal fastener 96 toward a second end 55 and from a second side 57 toward a first side 56. A second distal directional aperture 68 directs a second distal fastener 98 toward a first end 54 and from a first side 56 toward a second side 57. FIG. 9 shows an exemplary load sharing bone plate configured as a diaphyseal fracture bone plate consisting essentially of a body portion having a substantially uniform width and a load sharing extension on either end.

As shown in FIG. 10, an exemplary load sharing bone plate 14 has two load sharing extensions 18 and 18' that have a tapered thickness. The first load sharing extension 18 is configured with a flex feature 87 that may allow the extension to flex in response to a stress or load and thereby further reduce the stress concentration in the bone near the ends of the load sharing bone plate.

As shown in FIG. 11, a fractured long bone 13 has a metaphyseal fracture 27, a diaphyseal fracture 23 and an intra-articular fracture 25 that extends up into a joint. A long bone may be described as having epiphysis portions 28, 28' on either end of the bone and a diaphysis portion 22 configured therebetween. A load sharing bone plate, as described herein, may be used to secure and repair fractures in long bones as shown in FIG. 12-14, for example.

As shown in FIG. 12, an exemplary load sharing bone plate 14 is secured over a diaphyseal fracture 23 and has an articulation fixation portion 59 that is configured to be secured to an epiphysis portion 28 of the bone 12. The load sharing bone plate 14 has an elongated portion 49 that extends from the articulation fixation portion to the second end 55 of the bone plate, and the elongated portion has an aspect ratio of more than 3.0. The exemplary elongated portion shown in FIG. 12 comprises a body portion 48 that has a substantially uniform width and a stress sharing extension 18 configured at the second end 55 of the bone plate. Any number of fasteners 19 may be configured in an articulation fixation portion of a load sharing bone plate and the geometry of the articulation fixation portion may be any suitable shape to conform to the particular bone shape. The articular fixation portion 59 has a greater width than the elongated portion, as shown. An articular fixation portion is typically configured for attachment at or near a joint, such as juxta-articular or periarticular. A joint is typically wider than the long bone portion of the bone and/or may require fixation of a number of fractures in an around the joint. A wider articular fixation portion having a number of apertures therein enables greater flexibility in fixation of fractures in and around a joint.

As shown in FIG. 13, an exemplary load sharing bone plate 14 is secured over a metaphyseal fracture 27 and has an articulation fixation portion 59. The first and second proximal directional apertures, 62, 64 respectively, are configured on opposing sides of the metaphyseal fracture 27. A plurality of fasteners 19 are configured on the first end 54 of the bone plate and in the articulation fixation portion. A distal directional aperture 68 is configured proximal the second end 55 of the bone plate from the proximal directional apertures. The load sharing bone plate 14 has an elongated portion 49 that extends from the articulation fixation portion and the elongated portion has an aspect ratio of more than 3.0.

As shown in FIG. 14, an exemplary load sharing bone plate 14 is secured over a diaphyseal fracture 23 and a metaphyseal fracture 27 having an intra-articular extension 25 into the joint, or extending to the joint end 24 of the bone 12. The first and second proximal directional apertures, 62, 64 respectively, are configured on opposing sides of the diaphyseal fracture 23. A plurality of fasteners 19 are configured in the articulation fixation portion of the bone plate, and one or more of these fasteners may be directional apertures. In addition, one or more of these directional apertures may be oriented in relation to the metaphyseal fracture and/or intra-articular fracture to direct a fastener from one side of the fracture to the opposing side of the fracture. The fastener may have a head portion on one side of the fracture and an extended end secured into the bone on an opposing side of the fracture. A distal directional aperture 68 is configured proximal to the second end 55 of the bone plate from the proximal directional apertures. The load sharing bone plate 14 has an elongated portion 49 that extends from the articulation fixation portion, and the elongated portion has an aspect ratio of more than 3.0.

As shown in FIG. 15A, an exemplary load sharing bone plate 14 has a multi-aperture insert 110, configured in the articular fixation portion 59 of the bone plate, having two aperture insert portions 120, 130 each with two fastener apertures. The first insert portion is configured in a first aperture 67 in the bone plate and the second insert portion 130 is configured in a second aperture 67' in the bone plate. The first and second apertures 67, 67' are hourglass shaped and are distinct and separate from each other with bone plate material extending between the apertures. The first insert portion 120 is hourglass shaped and has a first fastener aperture 122 and a second fastener aperture 124 configured therein. The first and second fastener apertures 122, 124 are configured to direct a fastener in substantially the same direction as shown in FIG. 15B, where the large arrows indicate the directions that the fastener apertures will direct a fastener inserted therein. The second insert portion 130 is hourglass shaped and has a first fastener aperture 132 and a second fastener aperture 134 configured therein. Again, the first and second fastener apertures 132, 134 are configured to direct a fastener in substantially the same direction as shown in FIG. 15B. The length 182 of the articular fixation portion 59 is shown in FIG. 15B As shown in FIG. 16, the exemplary load sharing bone plate 14 shown in FIG. 15A has a multi-aperture insert 110, configured in the articular fixation portion 59 of the bone plate, having a coupling portion 140 extending between the two aperture insert portions. The coupling portion extends across the bone contact surface of the bone contact surface 52 of the bone plate. A recess 170 may be made in the surface of the load sharing bone plate 14 for the multi-aperture insert 110 and particularly for the coupling portion 110. The multi-aperture insert may be substantially flush with an outer surface, such as the bone contact surface, of a load sharing bone plate, whereby the multi-aperture insert does not extend out from the bone plate surface more than about 0.5 mm and preferably less than 0.25 mm. In another embodiment, a load sharing bone plate comprises a recess such that the multi-aperture insert is recessed into the surface of the bone plate, whereby the multi-aperture insert is configured below the surface of the bone plate. The multi-aperture insert has an insert surface 112 that may be substantially flat or planar or be configured to match the contours of the bone plate surface such that the multi-aperture insert is flush with the bone plate surface including any contoured surfaces. The insertion surface 113 of the bone plate is the surface configured for insertion of the multi-aperture insert and may comprise a recess 170 as shown such that the insert surface 112 is flush with the insertion surface 113. An insertion surface may be on a bone contact surface 52, as shown in FIG. 16 or on a top, or opposing surface of the bone plate.

As shown in FIG. 17, the exemplary load sharing bone plate 14 shown in FIGS. 15A and 16 has a coupling portion 140 that extends between the two aperture insert portions 120, 130. As shown in this embodiment, the multi-aperture insert is substantially flush with the bone contact surface 52 of the load sharing bone plate. The width 180 of the articular fixation portion 59 is shown in FIG. 17. The first aperture insert portion and the second aperture insert portion extend substantially through the thickness of the load sharing bone plate wherein they extend at least 75% through the thickness of the load sharing bone plate from the top surface, to the bone contact surface, and may extend at least 90%, or completely through the load sharing bone plate from the top surface to the bone contact surface.

As shown in FIG. 18, an exemplary load sharing bone plate 14 has a multi-aperture insert 110 configured in the articular fixation portion 59 of the bone plate. The multi-aperture insert has a first insert portion 120 configured in a first aperture 67 in the bone plate and a second insert portion 130 configured in a second aperture 67' in the bone plate. The first and second apertures 67, 67' are separate and distinct from each other. The first and second insert portions each have a single fastener aperture 122 and 132, respectively.

As shown in FIG. 19, the exemplary load sharing bone plate 14 shown in FIG. 18 has a multi-aperture insert 110 having a coupling portion 140 that extends between the two aperture insert portions 120, 130. The multi-aperture insert has an insert surface 112 that is generally hourglass shape and configured on the bone contact surface 52 of the bone plate.

As shown in FIG. 20, the exemplary load sharing bone plate 14, shown in FIGS. 18 and 19, has a coupling portion 140 that extends between the two aperture insert portions 120, 130. Each of the insert portions 120, 130, has an extended end that comprises flange 150, 150'. The flange is a flared extended end having an enlarged extended end diameter that tapers down to the smaller diameter.

As shown in FIG. 21, an exemplary multi-aperture insert 14 has two aperture insert portions 120, 130 coupled together by a coupling portion 140 that has a non-uniform thickness 146 between the first and second insert portions. When a first and/or second insert portion only has a single fastener aperture, a thicker or non-planar coupling portion may be configured between the two insert portions to provide more support and resistance to spinning of an insert portion that might be caused when a fastener is inserted therein. The exemplary insert portions 120 and 130 are substantially cylindrically shaped in FIG. 21.

As shown in FIG. 22, an exemplary multi-aperture insert 14 has two aperture insert portions 120, 130 coupled together by a coupling portion 140 that has a substantially uniform thickness and is planar. The first and second insert portions have directional fastener apertures 122 and 132. The fastener apertures have a fastener aperture axis 129 that is offset from the extended axis 138 of the insert portion by an offset angle 139. A fastener aperture axis extends in the direction that a fastener aperture is configured to direct a fastener and is generally parallel with length of the fastener aperture. An extended axis of an insert portion is aligned with the direction of the extended direction of an insert portion from the coupled end to the extended end. As shown in FIG. 22, the extended axis is substantially perpendicular to the plane of the coupling portion. Each of the fastener apertures has a beveled entry portion 136 at the extended ends of the insert portions. A beveled entry portion 136 may also be configured on the coupling portion end, or end of the insert portion proximal the coupling portion. The beveled entry portion allows a fastener to be countersunk into the insert portion. In an exemplary embodiment, a fastener may be countersunk into an insert portion wherein the top surface of the head of the fastener is substantially flush with the top surface of the bone plate or the top surface of the extended end of the insert portion. A flange 150 is configured around the multi-aperture insert 14 as shown in FIG. 22. The flange extends around the insert portions.

As shown in FIG. 23, an exemplary mufti-aperture insert 14 has two aperture insert portions 120, 130 and a coupling portion 14 that has a substantially uniform thickness therebetween. Each of the hourglass shaped insert portions have two fastener apertures that are configured to direct a fastener in an offset angle 128, or in a direction that is not parallel with the length axis 126 of the insert portion. The length axis of the insert portion is a line that is substantially perpendicular to the top and bottom openings of the fastener aperture and is generally perpendicular to the surfaces of the bone plate and extends through the thickness of the bone plate. The fastener aperture axis 129 is the axis or direction that the fastener aperture is configured to direct a fastener.

As shown in FIG. 24A, an exemplary multi-aperture 14 insert has two aperture insert portions 120, 130 coupled together by a coupling portion 140. Each of the insert portions have a flange 150 at the extended end 160 that is a flared extended end. As shown in FIG. 24A, the extended axis is parallel with the fastener aperture axis and therefore there is substantially no offset angle. It is to be understood that a fastener can be directed in an angle that is offset from the fastener aperture axis since the insert portion may be plastically deformed by the fastener.

As shown in FIG. 24B, an exemplary multi-aperture 14 insert has two aperture insert portions 120, 130 coupled together by a coupling portion 140. Each of the insert portions have a fastener aperture axis 129 that is offset by offset angle 128 to the length axis 126 of the insert portions and are aligned with the extended axis 138 of the insert portions. A fastener aperture axis extends generally along a centerline of the aperture through the insert portion. Note that the insert portions 120, 130 are generally aligned with the fastener aperture axis in the extended portion 142, 142' respectively, between the bone contact surface 52 and top surface 50.

A directional aperture may be configured in any suitable location on a load sharing bone plate, as described herein, to secure the bone plate to the bone.

It will be apparent to those skilled in the art that modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed:

1. A bone plate system comprising:
   a) a bone plate comprising:
      i) a top surface;
      ii) a bone contact surface;
      iii) a thickness between the top surface and bone contact surface;
      iv) a length from a first end to a second end;
      v) a width in a direction perpendicular to the length; and
      vi) an aperture extending through the bone plate from the top surface to the bone contact surface;
   b) a multi-aperture insert configured in said aperture of the bone plate such that it will not spin upon insertion of a fastener, said multi-aperture insert comprising:
      i) a first aperture insert portion comprising a fastener aperture and an extended end;
      ii) a second aperture insert portion comprising a fastener aperture and an extended end; and
      iii) a coupling portion that extends between the first aperture insert portion and the second aperture insert portion;
   wherein the multi-aperture insert is a monolithic component;
   wherein the first aperture insert portion and the second aperture insert portion extend at least 75% through the thickness of the bone plate; and
   wherein the first aperture insert portion comprises two fastener apertures and the second aperture insert portion comprises two fastener apertures.

2. The bone plate system of claim 1, wherein the coupling portion extends along the top surface of the bone plate.

3. The bone plate system of claim 1, wherein the first aperture insert portion and the second aperture insert portion extend completely through the thickness of the bone plate from the top surface to the bone contact surface.

4. The bone plate system of claim 1, wherein the coupling portion extends along the bone contact surface of the bone plate and the extended ends of the first and second aperture insert portions extend toward the top surface.

5. The bone plate system of claim 1, wherein the first aperture insert portion comprises a flange on the extended end of the first aperture insert portion.

6. The bone plate system of claim 1, wherein the multi-aperture insert comprises a flange that extends from the first aperture insert portion on an insertion surface of the multi-aperture insert, wherein the insertion surface is the surface configured to receive a fastener.

7. The bone plate system of claim 1, wherein at least one of the first aperture insert portion and the second aperture insert portion comprise a beveled entry portion.

8. The bone plate system of claim 1, wherein the bone plate comprises a recessed area for receiving the multi-aperture insert wherein an insert surface of the multi-aperture insert is substantially flush with an insertion surface of the bone plate.

9. The bone plate system of claim 8, wherein the recessed area is configured on the bone contact surface and the coupling portion is configured within said recess.

10. The bone plate system of claim 1, wherein the coupling portion has a substantially planar geometry and has no apertures therein.

11. The bone plate system of claim 1, wherein multi-aperture insert consists of a plastically deformable material and the bone plate consists of metal.

12. The bone plate system of claim 1, wherein each of the first aperture insert portion and second aperture insert portion has only one fastener aperture.

13. The bone plate system of claim 1, wherein at least one of the first aperture insert portion and second aperture insert portion comprises a plurality of fastener apertures, whereby two or more fasteners can be inserted through the aperture insert portion and attached to a bone to couple the bone plate to said bone.

14. The bone plate system of claim 1, wherein both of the first or second aperture insert portions comprise a fastener aperture configured to direct a fastener at an oblique angle with respect to said thickness of the bone plate.

15. The bone plate system of claim 14, wherein the oblique angle is at least 15 degrees.

16. The bone plate system of claim 1, further comprising a plurality of fasteners configured for insertion and attachment to said bone plate, wherein said plurality of fasteners are no more than 2.75 mm in shaft diameter.

17. The bone plate system of claim 1, wherein the bone plate further comprising a slotted aperture.

18. The bone plate system of claim 1, wherein the bone plate has an elongated portion having a substantially uniform width.

* * * * *